(12) United States Patent
Akatsuka et al.

(10) Patent No.: US 9,814,785 B2
(45) Date of Patent: Nov. 14, 2017

(54) HEPATITIS C VIRUS LIPOSOME VACCINE

(71) Applicants: Saitama Medical University, Iruma-gun, Saitama (JP); Japan as represented by the Director-General of National Institute of Infectious Diseases, Tokyo (JP); NOF Corporation, Tokyo (JP)

(72) Inventors: Toshitaka Akatsuka, Saitama (JP); Tetsuya Uchida, Tokyo (JP); Maiko Taneichi, Tokyo (JP); Ai Mikuma, Kawasaki (JP); Shoichi Yokoyama, Kawasaki (JP)

(73) Assignees: Saitama Medical University, Iruma (JP); Japan as represented by the Director-General of National Institute of Infectious Diseases, Tokyo (JP); NOF Corporation, Tokyo (JP)

( * ) Notice: Subject to any disclaimer, the term of this patent is extended or adjusted under 35 U.S.C. 154(b) by 0 days.

(21) Appl. No.: 14/831,539

(22) Filed: Aug. 20, 2015

(65) Prior Publication Data

US 2015/0343089 A1 Dec. 3, 2015

Related U.S. Application Data

(63) Continuation of application No. 13/821,718, filed as application No. PCT/JP2011/070408 on Sep. 7, 2011, now abandoned.

(30) Foreign Application Priority Data

Sep. 8, 2010 (JP) .................................. 2010-201160

(51) Int. Cl.
*A61K 47/48* (2006.01)
*C12N 7/00* (2006.01)
*A61K 31/7088* (2006.01)
*A61K 39/29* (2006.01)
*C12N 15/117* (2010.01)
*A61K 39/12* (2006.01)
*A61K 39/00* (2006.01)

(52) U.S. Cl.
CPC .... *A61K 47/48815* (2013.01); *A61K 31/7088* (2013.01); *A61K 39/12* (2013.01); *A61K 39/29* (2013.01); *A61K 47/48053* (2013.01); *C12N 7/00* (2013.01); *C12N 15/117* (2013.01); *A61K 2039/55555* (2013.01); *A61K 2039/572* (2013.01); *A61K 2039/6018* (2013.01); *C12N 2310/17* (2013.01); *C12N 2710/24143* (2013.01); *C12N 2770/24234* (2013.01)

(58) Field of Classification Search
None
See application file for complete search history.

(56) References Cited

U.S. PATENT DOCUMENTS

| | | |
|---|---|---|
| 5,709,995 A | 1/1998 | Chisari et al. |
| 6,555,114 B1 | 4/2003 | Leroux-Roels et al. |
| 2008/0038329 A1 | 2/2008 | Uchida et al. |
| 2009/0012004 A1 | 1/2009 | Sette et al. |
| 2010/0136098 A1 | 6/2010 | Uchida et al. |

FOREIGN PATENT DOCUMENTS

| | | |
|---|---|---|
| JP | H09-504534 A | 5/1997 |
| JP | H09-510455 A | 10/1997 |
| JP | 2002-507397 A | 3/2002 |
| JP | 2003-509465 A | 3/2003 |
| JP | 2003-524016 A | 8/2003 |
| JP | 2008-037831 A | 2/2008 |
| JP | 2008-509654 A | 4/2008 |
| WO | WO 1999/045954 A1 | 9/1999 |
| WO | WO 2001/021189 A1 | 3/2001 |
| WO | WO 2001/062776 A1 | 8/2001 |
| WO | WO 2005/118626 A2 | 12/2005 |
| WO | WO 2010/061924 A1 | 6/2010 |

OTHER PUBLICATIONS

Jiao et al., Journal of General Virology (2004), 85, 1545-1553.*
Arribillaga et al., *Vaccine*, 21: 202-210 (2002).
Chua et al., *Vaccine*, 26: 4866-4875 (2008).
Dittmer et al., *Current Opinion in Microbiology*, 6: 472-477 (2003).
Engler et al., *Vaccine*, 23: 58-68 (2004).
Folgori et al., *Nature Medicine*, 12(2): 190-197 (2006).
Houghton, *Immunological Reviews*, 239: 99-108 (2011).
Ito et al., *Hepatology Research*, 36: 294-300 (2006).
Kolykhalov et al., *Science*, 277: 570-574 (1997).
Krieg, *Biochimica et Biophysica Acta*, 1489: 107-116 (1999).
Makimura et al., *Vaccine*, 14(1): 28-34 (1996).
Moriya et al., *Vaccine*, 20: 789-796 (2002).
Ohnisi et al., *Journal of Virology*, 68(6): 4075-4079 (1994).
Ohno et al., *Viral Immunology*, 19(3): 458-467 (2006).

(Continued)

*Primary Examiner* — Marcela M Cordero Garcia
*Assistant Examiner* — Catherine Mader
(74) *Attorney, Agent, or Firm* — Leydig, Voit & Mayer, Ltd.

(57) ABSTRACT

The invention provides a method for the prophylaxis or treatment of hepatitis C in a mammal with a peptide-bound liposome wherein the peptide contains a partial amino acid sequence having a length of not less than 9 amino acids in the amino acid sequence of hepatitis C virus NS3 protein, has a length of 9 to 11 amino acids, and is capable of inducing cytotoxic T lymphocytes; the liposome contains a phospholipid containing an acyl group having 14 to 24 carbon atoms and one unsaturated bond or a hydrocarbon group having 14 to 24 carbon atoms and one unsaturated bond, and a liposome stabilizer; and the peptide is bound to the surface of the liposome. The invention also provides a cytotoxic T lymphocyte activator containing the peptide-bound liposome, as well as a hepatitis C virus vaccine.

14 Claims, 10 Drawing Sheets

(56) References Cited

OTHER PUBLICATIONS

Pascolo et al., *J. Exp. Med.*, 185(12): 2043-2051 (1997).
Sarobe et al., *J. Clin. Invest.*, 102(6): 1239-1248 (1998).
Schlaphoff et al., *Vaccine*, 25: 6793-6806 (2007).
Shirai et al., *Journal of Virology*, 66(7): 4098-4106 (1992).
Shirai et al., *Journal of Virology*, 68(5): 3334-3342 (1994).
Takagi et al., *Biochemical and Biophysical Research Communications*, 430: 183-189 (2013).
Takagi et al., *Clinical and Vaccine Immunology*, 16(10): 1383-1392 (2009).
Uchida, *Heisei 13 to 15 Nendo Soyaku to Human Science Kenkyu Sogo Kenkyu Hokokusho*, 66-70 (Sep. 2004).
Urbani et al., *Hepatology*, 33: 1533-1543 (2001).
Wedemeyer et al., *Vaccine*, 27: 5142-5151 (2009).
Youn et al., *Journal of Virology*, 82(21): 10896-10905 (2008).
Zubkova et al., *Vaccine*, 27:2594-2602 (2009).
Japanese Patent Office, International Search Report in International Patent Application No. PCT/JP2011/070408 (dated Oct. 25, 2011).
The International Bureau of WIPO, International Preliminary Report on Patentability in International Application No. PCT/JP2011/070408 (dated Apr. 9, 2013).
Gerlach et al., *Journal of Virology*, 79(19):12425-12433 (2005).
Japanese Patent Office, Office Action in Japanese Patent Application No. 2012-533011 (dated Oct. 13, 2015).

\* cited by examiner

Fig. 3
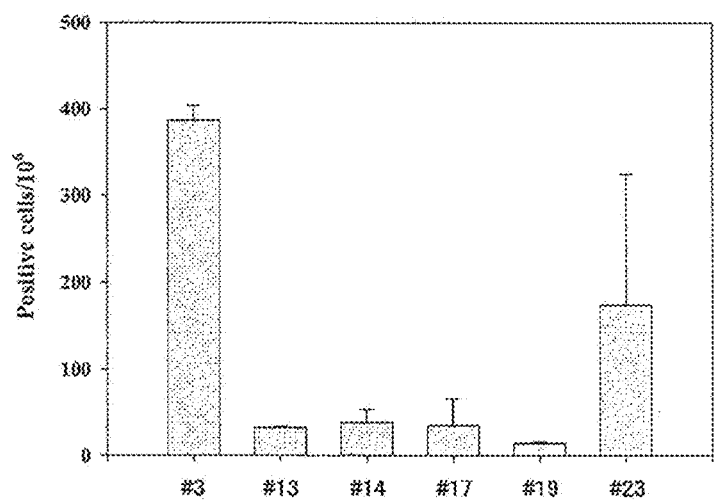
ELISPOT
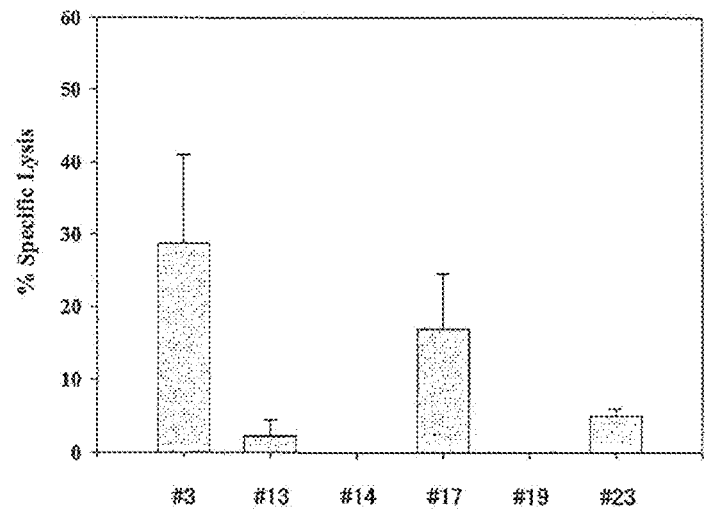
$^{51}$Cr-release

Fig. 4
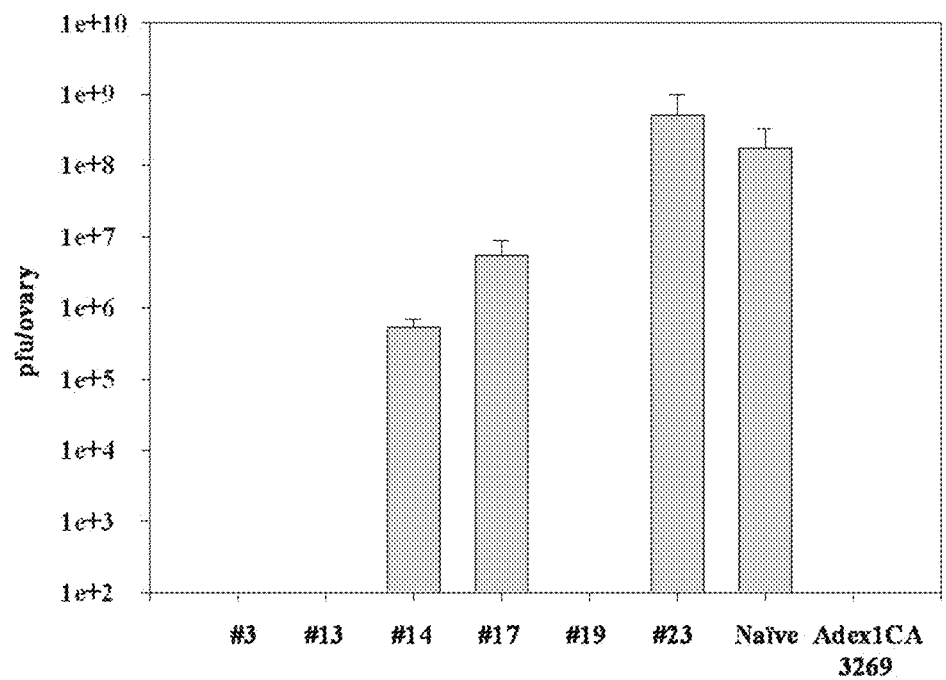
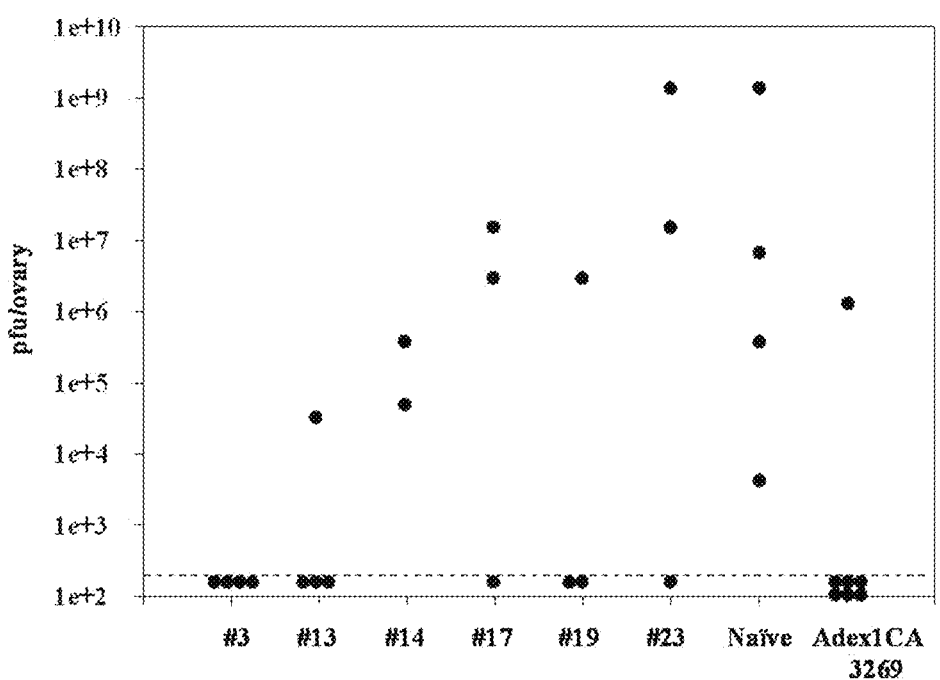

SEQUENCE LISTING

<160> NUMBER OF SEQ ID NOS: 30

<210> SEQ ID NO 1
<211> LENGTH: 9
<212> TYPE: PRT
<213> ORGANISM: Hepatitis C virus

<400> SEQUENCE: 1

Tyr Met Asn Thr Pro Gly Leu Pro Val
1               5

<210> SEQ ID NO 2
<211> LENGTH: 9
<212> TYPE: PRT
<213> ORGANISM: Hepatitis C virus

<400> SEQUENCE: 2

Ala Met Phe Asp Ser Ser Val Leu Cys
1               5

<210> SEQ ID NO 3
<211> LENGTH: 9
<212> TYPE: PRT
<213> ORGANISM: Hepatitis C virus

<400> SEQUENCE: 3

Ile Met Thr Cys Met Ser Ala Asp Leu
1               5

<210> SEQ ID NO 4
<211> LENGTH: 9
<212> TYPE: PRT
<213> ORGANISM: Hepatitis C virus

<400> SEQUENCE: 4

Tyr Leu Asn Thr Pro Gly Leu Pro Val
1               5

<210> SEQ ID NO 5
<211> LENGTH: 9
<212> TYPE: PRT
<213> ORGANISM: Hepatitis C virus

<400> SEQUENCE: 5

Gly Met Phe Asp Ser Ser Val Leu Cys
1               5

<210> SEQ ID NO 6
<211> LENGTH: 9
<212> TYPE: PRT
<213> ORGANISM: Hepatitis C virus

<400> SEQUENCE: 6

Ile Met Ala Cys Met Ser Ala Asp Leu
1               5

<210> SEQ ID NO 7
<211> LENGTH: 9
<212> TYPE: PRT
<213> ORGANISM: Hepatitis C virus

<400> SEQUENCE: 7

Gly Ser Pro Ile Thr Tyr Ser Thr Tyr
1               5

<210> SEQ ID NO 8
<211> LENGTH: 9
<212> TYPE: PRT
<213> ORGANISM: Hepatitis C virus

<400> SEQUENCE: 8

```
Arg Leu Gly Ala Val Gln Asn Glu Val
1               5

<210> SEQ ID NO 9
<211> LENGTH: 9
<212> TYPE: PRT
<213> ORGANISM: Hepatitis C virus

<400> SEQUENCE: 9

Tyr Leu Val Thr Arg His Ala Asp Val
1               5

<210> SEQ ID NO 10
<211> LENGTH: 9
<212> TYPE: PRT
<213> ORGANISM: Hepatitis C virus

<400> SEQUENCE: 10

Gly Leu Pro Val Cys Gln Asp His Leu
1               5

<210> SEQ ID NO 11
<211> LENGTH: 9
<212> TYPE: PRT
<213> ORGANISM: Hepatitis C virus

<400> SEQUENCE: 11

Ile Ile Cys Asp Glu Cys His Ser Thr
1               5

<210> SEQ ID NO 12
<211> LENGTH: 9
<212> TYPE: PRT
<213> ORGANISM: Hepatitis C virus

<400> SEQUENCE: 12

Thr Leu His Gly Pro Thr Pro Leu Leu
1               5

<210> SEQ ID NO 13
<211> LENGTH: 9
<212> TYPE: PRT
<213> ORGANISM: Hepatitis C virus

<400> SEQUENCE: 13

Gln Met Trp Lys Cys Leu Ile Arg Leu
1               5

<210> SEQ ID NO 14
<211> LENGTH: 9
<212> TYPE: PRT
<213> ORGANISM: Hepatitis C virus

<400> SEQUENCE: 14

Phe Ser Leu Asp Pro Thr Phe Thr Ile
1               5

<210> SEQ ID NO 15
<211> LENGTH: 9
<212> TYPE: PRT
<213> ORGANISM: Hepatitis C virus

<400> SEQUENCE: 15

Cys Leu Ile Arg Leu Lys Pro Thr Leu
1               5
```

-continued

<210> SEQ ID NO 16
<211> LENGTH: 9
<212> TYPE: PRT
<213> ORGANISM: Hepatitis C virus

<400> SEQUENCE: 16

Val Leu Asn Pro Ser Val Ala Ala Thr
1 5

<210> SEQ ID NO 17
<211> LENGTH: 9
<212> TYPE: PRT
<213> ORGANISM: Hepatitis C virus

<400> SEQUENCE: 17

Ser Val Ile Asp Cys Asn Thr Cys Val
1 5

<210> SEQ ID NO 18
<211> LENGTH: 9
<212> TYPE: PRT
<213> ORGANISM: Hepatitis C virus

<400> SEQUENCE: 18

Gly Leu Asp Val Ser Val Ile Pro Thr
1 5

<210> SEQ ID NO 19
<211> LENGTH: 9
<212> TYPE: PRT
<213> ORGANISM: Hepatitis C virus

<400> SEQUENCE: 19

Gly Val Phe Thr Gly Leu Thr His Ile
1 5

<210> SEQ ID NO 20
<211> LENGTH: 9
<212> TYPE: PRT
<213> ORGANISM: Hepatitis C virus

<400> SEQUENCE: 20

Lys Val Leu Val Leu Asn Pro Ser Val
1 5

<210> SEQ ID NO 21
<211> LENGTH: 9
<212> TYPE: PRT
<213> ORGANISM: Hepatitis C virus

<400> SEQUENCE: 21

Cys Met Ser Ala Asp Leu Glu Val Val
1 5

<210> SEQ ID NO 22
<211> LENGTH: 9
<212> TYPE: PRT
<213> ORGANISM: Hepatitis C virus

<400> SEQUENCE: 22

Gly Leu Phe Arg Ala Ala Val Cys Thr
1 5

```
<210> SEQ ID NO 23
<211> LENGTH: 9
<212> TYPE: PRT
<213> ORGANISM: Hepatitis C virus

<400> SEQUENCE: 23

Lys Leu Val Ala Leu Gly Ile Asn Ala
1               5

<210> SEQ ID NO 24
<211> LENGTH: 9
<212> TYPE: PRT
<213> ORGANISM: Hepatitis C virus

<400> SEQUENCE: 24

Leu Leu Cys Pro Ala Gly His Ala Val
1               5

<210> SEQ ID NO 25
<211> LENGTH: 9
<212> TYPE: PRT
<213> ORGANISM: Hepatitis C virus

<400> SEQUENCE: 25

Arg Leu Val Val Leu Ala Thr Ala Thr
1               5

<210> SEQ ID NO 26
<211> LENGTH: 9
<212> TYPE: PRT
<213> ORGANISM: Hepatitis C virus

<400> SEQUENCE: 26

Phe Leu Ala Thr Cys Ile Asn Gly Val
1               5

<210> SEQ ID NO 27
<211> LENGTH: 9
<212> TYPE: PRT
<213> ORGANISM: Hepatitis C virus

<400> SEQUENCE: 27

Ala Val Gly Leu Phe Arg Ala Ala Val
1               5

<210> SEQ ID NO 28
<211> LENGTH: 9
<212> TYPE: PRT
<213> ORGANISM: Hepatitis C virus

<400> SEQUENCE: 28

Leu Leu Gly Cys Ile Ile Thr Ser Leu
1               5

<210> SEQ ID NO 29
<211> LENGTH: 29
<212> TYPE: DNA
<213> ORGANISM: Artificial Sequence
<220> FEATURE:
<223> OTHER INFORMATION: Sense primer

<400> SEQUENCE: 29
gccggatcca tggtctccaa ggggtggag                                    29

<210> SEQ ID NO 30
```

```
<211> LENGTH: 25
<212> TYPE: DNA
<213> ORGANISM: Artificial Sequence
<220> FEATURE:
<223> OTHER INFORMATION: Antisense primer

<400> SEQUENCE: 30
tcacgtgacg acctccaggt cggcc                                              25
```

HEPATITIS C VIRUS LIPOSOME VACCINE

CROSS-REFERENCE TO RELATED APPLICATIONS

This patent application is a continuation of U.S. patent application Ser. No. 13/821,718, filed on Apr. 5, 2013, which is the U.S. national phase of International Patent Application PCT/JP2011/070408, filed on Sep. 7, 2011, which claims the benefit of Japanese Patent Application No. 2010-201160, filed Sep. 8, 2010, which are incorporated by reference in their entireties herein.

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 4,978 bytes ASCII (Text) file named "721558SequenceListing.txt," created Aug. 18, 2015.

TECHNICAL FIELD

The present invention relates to a peptide-bound liposome useful as a hepatitis C virus vaccine, the peptide, and use thereof.

BACKGROUND ART

Hepatitis C is a viral hepatitis developed by infection with hepatitis C virus. Infection with hepatitis C virus sometimes cures inartificially; however, in many cases, it progresses to chronic hepatitis when left unattended. When the state of chronic hepatitis continues, it progresses to cirrhosis, and further, the risk of developing liver cancer increases. There are even reports stating that about 80% of the cause of liver cancer is hepatitis C.

In the treatment of hepatitis C, interferon therapy achieves a certain treatment outcome. Depending on the genotype of hepatitis C virus, however, interferon therapy may be less effective (for example, type 1b high viral load case). Therefore, the development of a treatment method effective for a broader range of patients has been desired.

Virus-infected cells expose, on the surfaces thereof, a major histocompatibility antigen complex (MHC) presenting partial peptide of a viral internal protein. If cytotoxic T lymphocytes ($CD8^+$ T cells, cytotoxic lymphocytes: CTL) capable of specifically killing virus-infected cells exhibiting these features can be induced, the replication, and hence proliferation and spread of the virus, can be prevented effectively.

Hepatitis C virus is known to have low immunogenicity as compared to other viruses. Thus, a method of inducing CTL by utilizing an epitope having comparatively high immunogenicity, which is present in hepatitis C virus antigen, has been considered.

Patent document 1 discloses a peptide derived from the protein of hepatitis C virus, which induces an HLA-restricted CTL response in an immunized host. Patent document 2 discloses an immunogenic peptide of hepatitis C virus capable of binding to HLA A2.1, and an induction method of cytotoxic T lymphocyte by a composition containing the peptide. However, it is unknown whether these peptides are effective for the actual treatment or prophylaxis of hepatitis C.

On the other hand, as a method for potentiating an immune response in the body, a method using a liposome preparation is known.

Patent Document 3 discloses a method of preparing a T cell activator capable of efficiently and specifically augmenting CTL to kill pathogen-infected cells or cancer cells using an antigen-bound liposome, and useful for the prevention or treatment of infectious diseases and cancers.

In addition, patent document 4 describes that an antigen epitope especially effective for the preparation of cytotoxic T lymphocytes was found in a highly conserved internal protein sequence of avian influenza virus, and that a liposome bound, on its surface, with a peptide containing the epitope can extremely strongly induce antigen specific cytotoxic T lymphocytes.

DOCUMENT LIST

Patent Documents patent document 1: WO2005/118626
patent document 2: US-B-2009/0012004
patent document 3: JP-A-2008-37831
patent document 4: WO2010/061924

SUMMARY OF THE INVENTION

Problems to be Solved by the Invention

The problem to be solved by the present invention is provision of a vaccine capable of inducing cytotoxic T lymphocyte efficiently, and having a treatment effect or prophylactic effect on hepatitis C.

Means of Solving the Problems

In view of the above-mentioned problem, the present inventors have conducted intensive studies and found that the cytotoxic T lymphocyte induction intensity of an antigen peptide not bound to a liposome and that of an antigen peptide bound to a liposome are not in parallel relationship, and an antigen peptide showing a weak cytotoxic T lymphocyte induction activity when it is not bound to a liposome may be able to extremely strongly induce cytotoxic T lymphocyte when it is bound to a liposome. Thus, they have searched for an antigen epitope, which is particularly effective for the induction of cytotoxic T lymphocyte by using a liposome, in the NS3 protein sequence of hepatitis C virus, and found some superior antigen epitopes. Furthermore, they have found that vaccination with a liposome bound with a peptide containing this epitope enables extremely strong induction of antigen-specific cytotoxic T lymphocytes and the treatment or prophylaxis of hepatitis C, which resulted in the completion of the present invention.

Accordingly, the present invention provides the following.

[1] A peptide-bound liposome wherein the peptide comprises a partial amino acid sequence having a length of not less than 9 amino acids in the amino acid sequence of hepatitis C virus NS3 protein,
has a length of 9 to 11 amino acids, and
is capable of inducing cytotoxic T lymphocytes;
the liposome comprises a phospholipid containing an acyl group having 14 to 24 carbon atoms and one unsaturated bond or a hydrocarbon group having 14 to 24 carbon atoms and one unsaturated bond, and a liposome stabilizer; and
the peptide is bound to the surface of the liposome.

[2] The peptide-bound liposome according to [1], wherein the phospholipid is a phospholipid containing an acyl group having 14 to 24 carbon atoms and one unsaturated bond.

[3] The peptide-bound liposome according to [1], wherein the acyl group is an oleoyl group.

[4] The peptide-bound liposome according to [1], wherein the phospholipid is at least one selected from diacylphosphatidylserine, diacylphosphatidylglycerol, diacylphosphatidic acid, diacylphosphatidylcholine, diacylphosphatidylethanolamine, succinimidyl-diacylphosphatidylethanolamine, and maleimido-diacylphosphatidylethanolamine.

[5] The peptide-bound liposome according to [1], wherein the liposome stabilizer is cholesterol.

[6] The peptide-bound liposome according to [1], wherein the peptide is bound to a phospholipid containing an acyl group having 14 to 24 carbon atoms and one unsaturated bond or a hydrocarbon group having 14 to 24 carbon atoms and one unsaturated bond, which phospholipid is contained in a phospholipid membrane constituting the liposome.

[7] The peptide-bound liposome according to [1], wherein the liposome has the following composition:
(A) a phospholipid containing an acyl group having 14 to 24 carbon atoms and one unsaturated bond or a hydrocarbon group having 14 to 24 carbon atoms and one unsaturated bond 1 to 99.8 mol %;
(B) a liposome stabilizer 0.2 to 75 mol %.

[8] The peptide-bound liposome according to [1], wherein the liposome has the following composition:
(I) an acidic phospholipid containing an acyl group having 14 to 24 carbon atoms and one unsaturated bond or a hydrocarbon group having 14 to 24 carbon atoms and one unsaturated bond 1 to 85 mol %;
(II) a neutral phospholipid containing an acyl group having 14 to 24 carbon atoms and one unsaturated bond or a hydrocarbon group having 14 to 24 carbon atoms and one unsaturated bond 0.01 to 80 mol %;
(III) a phospholipid containing an acyl group having 14 to 24 carbon atoms and one unsaturated bond or a hydrocarbon group having 14 to 24 carbon atoms and one unsaturated bond, which is bound with a peptide 0.2 to 80 mol %;
(IV) a liposome stabilizer 0.2 to 75 mol %.

[9] The peptide-bound liposome according to [1], wherein the partial amino acid sequence is an amino acid sequence shown by any of SEQ ID NOs: 1-3, 5 and 6.

[10] A cytotoxic T lymphocyte activator comprising the peptide-bound liposome according to [1].

[11] The cytotoxic T lymphocyte activator according to [10], further comprising CpG-DNA.

[12] A hepatitis C virus vaccine comprising the peptide-bound liposome according to [1].

[13] The hepatitis C virus vaccine according to [12], further comprising CpG-DNA.

[14] The hepatitis C virus vaccine according to [12], which is for the treatment of hepatitis C.

[15] The hepatitis C virus vaccine according to [12], which is for the prophylaxis of hepatitis C.

[16] A peptide comprising an amino acid sequence shown by SEQ ID NO: 1 or 2, having a length of 9-11 amino acids, and capable of inducing cytotoxic T lymphocyte.

[17] The peptide-bound liposome according to [1], which is for use for the prophylaxis or treatment of hepatitis C.

[18] A method for the prophylaxis or treatment of hepatitis C in a mammal, comprising administering a prophylactically or therapeutically effective amount of the peptide-bound liposome according to [1] to the mammal.

[19] Use of the peptide-bound liposome according to [1] for the production of a hepatitis C virus vaccine.

Effect of the Invention

Using the peptide-bound liposome or peptide of the present invention, cytotoxic T lymphocyte can be efficiently induced, which is useful for the treatment or prophylaxis of hepatitis C. In addition, using the peptide-bound liposome or peptide of the present invention, a hepatitis C virus vaccine with highly broad utility and effective for hepatitis C virus of both genotypes of type 1a and type 1b can be provided.

BRIEF DESCRIPTION OF THE DRAWINGS

FIG. 3 shows the results of immunogenicity of each peptide, which was examined using a peptide-bound liposome prepared from each peptide. The number of IFN-γ productive cells in the stimulation with each peptide-bound liposome was quantified by the ELISPOT method, and the cytotoxicity of cytotoxic T lymphocyte was measured by $^{51}Cr$ release method.

FIG. 4 shows the vaccine effect of peptide-bound liposomes prepared from respective peptides. Each graph shows the titer of the virus contained in the ovary. upper panel: bar graph; lower panel: individual data plot. The broken line shows the lower detection limit.

DESCRIPTION OF EMBODIMENTS

1. Peptide-Bound Liposome

Figure 1:
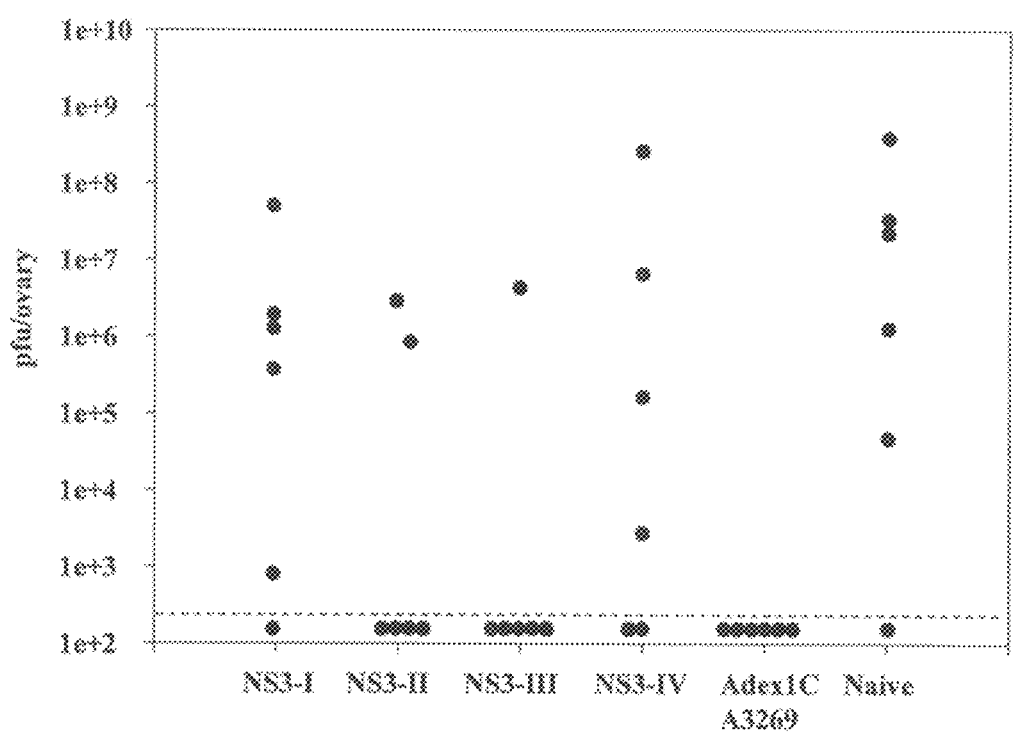
FIG. 1 shows the vaccine effect of a peptide-bound liposome. Each graph shows the titer of the virus contained in the ovary. Of 25 candidate peptides, 24 peptides except one which was poorly soluble in water were divided into 4 pools (NS3-I to IV), peptide-bound liposomes were prepared using each pool, and the vaccine effect was measured. The results using Adex1CA3269 are shown as positive control, and the results without immunization (Naive) are shown as negative control. The broken line shows the lower detection limit.

The present invention provides a peptide-bound liposome wherein the peptide comprises a partial amino acid sequence having a length of not less than 9 amino acids in the amino acid sequence of hepatitis C virus NS3 protein (preferably amino acid sequence shown by any of SEQ ID NOs: 1-3, 5 and 6), has a length of 9 to 11 amino acids, and is capable of inducing cytotoxic T lymphocytes;
the liposome comprises a phospholipid containing an acyl group having 14 to 24 carbon atoms and one unsaturated bond or a hydrocarbon group having 14 to 24 carbon atoms and one unsaturated bond, and a liposome stabilizer; and
the peptide is bound to the surface of the liposome.

The present invention has been completed based on the finding, in hepatitis C virus antigen, of an epitope sequence having a length of not less than 9 amino acids (epitope sequence of the present invention), in the amino acid sequence of hepatitis C virus NS3 protein, as an epitope having an activity to strongly induce cytotoxic T cells when bound to a surface of a liposome to be described in detail below. The epitope sequence of the present invention is preferably an epitope sequence shown by any of SEQ ID NOs: 1-3, 5 and 6, from the aspects of effectiveness of vaccine when bound to a liposome.

Amino acid sequences shown by SEQ ID NOs: 1-6 correspond to partial sequences present in the amino acid sequences of hepatitis C virus NS3 protein.

The peptides consisting of the amino acid sequences include, for example, peptides consisting of the corresponding epitope sequences in the same antigen of different virus strains, as shown below.

```
(1a strain)              (SEQ ID NO: 1)
YMNTPGLPV (1b strain)              (SEQ ID NO: 4)
→YLNTPGLPV (J1 strain)              (SEQ ID NO: 2)
AMFDSSVLC (1a strain)              (SEQ ID NO: 5)
→GMFDSSVLC (1a strain)              (SEQ ID NO: 3)
IMTCMSADL (J1 strain)              (SEQ ID NO: 6)
→IMACMSADL
```

A peptide containing the epitope sequence of the present invention (epitope peptide of the present invention) can induce cytotoxic T lymphocytes. "Inducing cytotoxic T lymphocytes" means that when a mammal (e.g., humans, transgenic mice and the like) is immunized with an antigen, the number and/or activity (e.g., cytotoxic activity) of cytotoxic T lymphocytes that specifically recognize the antigen rises in the body of the mammal.

The length of the peptide contained in the peptide-bound liposome of the present invention is not particularly limited, and is normally 9 to 11 amino acids, preferably 9 to 10 amino acids, and more preferably 9 amino acids. When the length of the peptide is 10 amino acids or more, the peptide has an additional sequence on the N-terminal side and/or C-terminal side of the epitope sequence of the present invention. The length and amino acid sequence of the additional sequence is not particularly limited, as far as the above-described characteristics of the peptide are not affected. For example, the additional sequence can be an amino acid sequence actually existing adjacent to a partial sequence corresponding to any one of SEQ ID NO:1 to 6 in the amino acid sequences of the NS3 protein of a hepatitis C virus. Particularly preferred is a residue capable of overcoming the selection of an antigen to be presented, due to personal differences in MHC (polymorphism) when the above-described peptide forms a major histocompatibility antigen complex (MHC) in cells.

The peptide contained in the peptide-bound liposome of the present invention can be prepared by, for example, a known technique for peptide synthesis, such as liquid phase synthesis or solid phase peptide synthesis. Alternatively, a transformant (*Escherichia coli* and the like) incorporating an expression vector capable of expressing the peptide is cultured, and the peptide is isolated from the culture by a commonly known technique for purification such as an affinity column, whereby the peptide can be produced. An expression vector capable of expressing the peptide can be constructed by ligating a polynucleotide that encodes the peptide downstream of a promoter in an appropriate expression vector using a commonly known technique for gene engineering.

The phospholipid membrane constituting the liposome moiety of the peptide-bound liposome of the present invention has a structure wherein a phospholipid, which is an amphoteric surfactant, forms an interface with the polar group thereof facing the water phase side, and the hydrophobic group thereof facing the opposite side of the interface. Here, a liposome refers to a phospholipid double membrane having a closed space.

The peptide contained in the peptide-bound liposome of the present invention is capable of binding to the surface of a liposome via a functional group possessed thereby. As functional groups in the peptide used for binding to the surface of a liposome, an amino group, a thiol group, a carboxyl group, a hydroxy group, a disulfide group, a hydrophobic group consisting of a hydrocarbon group (alkyl group and the like) having a methylene chain, and the like can be mentioned. These groups are capable of allowing the peptide to bind to the surface of a liposome, by a covalent bond for an amino group, a thiol group, a carboxyl group, a hydroxy group and a disulfide group, by an ionic bond for an amino group and a carboxyl group, and by a hydrophobic bond between hydrophobic groups. The peptide binds to the surface of a liposome preferably via an amino group, a carboxyl group or a thiol group.

It is desirable that the phospholipid membrane constituting the liposome have a functional group such as an amino group, a succinimide group, a maleimide group, a thiol group, a carboxyl group, a hydroxy group, a disulfide group, or a hydrophobic group consisting of a hydrocarbon group (alkyl group and the like) having a methylene chain, so that the peptide contained in the peptide-bound liposome of the present invention may stably bind to a liposome via a functional group possessed by the peptide. The functional group possessed by the phospholipid membrane constituting the liposome is preferably an amino group, a succinimide group or a maleimide group. A combination of a functional group possessed by the peptide and a functional group possessed by the phospholipid membrane constituting the liposome, involved in the binding of the peptide to the liposome, can be optionally chosen, as far as the effect of the present invention is not influenced; as preferable combinations, an amino group and an aldehyde group, an amino group and an amino group, an amino group and a succinimide group, a thiol group and a maleimide group and the like can be mentioned. Ionic bonds and hydrophobic bonds are preferable from the viewpoint of the ease of preparation of a peptide-bound liposome because of the convenient procedure of binding of the peptide to the liposome, and covalent bonds are preferable in view of the binding stability of the peptide on the liposome surface or storage stability in practical use of the peptide-bound liposome. A feature of the peptide-bound liposome of the present invention resides in the fact that the peptide having an excellent cytotoxic T lymphocyte activating effect is bound to the surface of the liposome being a constituent thereof. Therefore, in practical settings, it is preferable in view of enhancement of the effect of the present invention that, even after being administered to a living organism by the act of injection, for example, the peptide be stably bound to the surface of the liposome. From this viewpoint, the bond between the peptide and the liposome is preferably a covalent bond.

The phospholipid membrane constituting the liposome moiety of the peptide-bound liposome of the present invention comprises a phospholipid containing an acyl group having 14 to 24 carbon atoms and one unsaturated bond or a hydrocarbon group having 14 to 24 carbon atoms and one unsaturated bond, and a liposome stabilizer.

In the phospholipid containing an acyl group having 14 to 24 carbon atoms and one unsaturated bond, the number of carbon atoms of the acyl group is preferably 16 to 22, more preferably 18 to 22, and most preferably 18. As the acyl group, specifically, a palmitoleoyl group, an oleoyl group, an erucoyl group and the like can be mentioned, and an oleoyl group is most preferable.

In the phospholipid having a hydrocarbon group having 14 to 24 carbon atoms and one unsaturated bond, the number of carbon atoms of the hydrocarbon group is preferably 16 to 22, more preferably 18 to 22, and most preferably 18. As the hydrocarbon group specifically, a tetradecenyl group, a hexadecenyl group, an octadecenyl group, a C20 monoene group, a C22 monoene group, a C24 monoene group and the like can be mentioned.

The unsaturated acyl groups or unsaturated hydrocarbon groups that bind to the 1-position and 2-position of the glycerin residue present in the phospholipid may be identical or different. From the viewpoint of industrial productivity, it is preferable that the groups at the 1-position and 2-position be identical.

As the phospholipid, a phospholipid containing an acyl group having 14 to 24 carbon atoms and one unsaturated bond is preferably used.

It is an object of the present invention to efficiently and specifically augment cytotoxic T lymphocytes (CD8$^+$ T cells, CTL) for killing cells infected with hepatitis C virus. In view of enhancement of CTL activity to a practically sufficient level, it is preferable that the phospholipid have an acyl group having 14 to 24 carbon atoms and one unsaturated bond. If the number of carbon atoms of the acyl group is less than 13, the liposome stability worsens, or the CTL activity enhancing effect is insufficient in some cases. If the number of carbon atoms of the acyl group exceeds 24, the liposome stability worsens in some cases.

As the phospholipid containing an acyl group having 14 to 24 carbon atoms and one unsaturated bond or a hydrocarbon group having 14 to 24 carbon atoms and one unsaturated bond, an acidic phospholipid, a neutral phospholipid, a reactive phospholipid having a functional group capable of binding a peptide and other kinds can be mentioned. These can be chosen as appropriate with respect to the kind and ratio thereof according to various requirements.

As the acidic phospholipid, phosphatidylserine, phosphatidylglycerol, phosphatidic acid, phosphatidylinositol and the like can be used. In view of enhancement of CTL activity to a practically sufficient level, industrial supply, quality for pharmaceutical use and the like, diacylphosphatidylserine, diacylphosphatidylglycerol, diacylphosphatidic acid, and diacylphosphatidylinositol having an acyl group having 14 to 24 carbon atoms and one unsaturated bond are preferably used. An acidic phospholipid confers an anionic ionized group to the surface of a liposome, thus conferring a negative zeta potential to the liposome surface. For this reason, the liposome acquires a charge-based repulsive force, and can exist as a stable preparation in an aqueous solvent. Hence, an acidic phospholipid is important in assuring liposome stability when the peptide-bound liposome of the present invention is present in an aqueous solvent.

As the neutral phospholipid, for example, phosphatidylcholine and the like can be used. A neutral phospholipid that can be used in the present invention, as far as enhancement of CTL activity, an object of the present invention, is accomplished, can be chosen as appropriate with respect to the kind and amount thereof. A neutral phospholipid, compared with an acidic phospholipid and a phospholipid with the peptide of the present invention bound thereto, is more highly functional in stabilizing liposomes, thus being capable of improving membrane stability. From this viewpoint, it is preferable that the phospholipid membrane constituting the liposome moiety of the peptide-bound liposome of the present invention comprise a neutral phospholipid. Provided that sufficient contents of an acidic phospholipid used to achieve a CTL activity enhancing effect, a reactive phospholipid for peptide binding and a liposome stabilizer are assured, the amount of neutral phospholipid used can be determined.

In the peptide-bound liposome of the present invention, the peptide of the present invention binds to the surface of the liposome by binding to a phospholipid containing an acyl group having 14 to 24 carbon atoms and one unsaturated bond or a hydrocarbon group having 14 to 24 carbon atoms and one unsaturated bond, contained in the phospholipid membrane constituting the liposome.

As a phospholipid for this peptide binding, a reactive phospholipid having a functional group capable of having the peptide of the present invention bound thereto is used. A reactive phospholipid containing an acyl group having 14 to 24 carbon atoms and one unsaturated bond or a hydrocarbon group having 14 to 24 carbon atoms and one unsaturated bond can be chosen as appropriate with respect to the kind and ratio thereof according to various requirements. As with the above-described phospholipids, for the reactive phospholipid, it is undesirable that the number of carbon atoms of the unsaturated acyl group or unsaturated hydrocarbon group contained in the phospholipid exceeds 24 or is less than 14.

As the reactive phospholipid, phosphatidylethanolamine or a terminal-modified derivative thereof can be mentioned. Phosphatidylglycerol, phosphatidylserine, phosphatidic acid, phosphatidylinositol and terminal-modified derivatives thereof can also be used as the reactive phospholipid. From the viewpoints of industrial availability, the simplicity of the step of binding to the peptide of the present invention, percent yield and the like, it is preferable that phosphatidylethanolamine or a terminal-modified derivative thereof be used. Phosphatidylethanolamine has an amino group capable of having the peptide of the present invention bound to an end thereof. Furthermore, in view of enhancement of CTL activity to a practically sufficient level, stability in liposomes, industrial supply, quality for pharmaceutical use and the like, diacylphosphatidylethanolamine having an acyl group having 14 to 24 carbon atoms and one unsaturated bond, or a terminal-modified derivative thereof is most preferably used.

Diacylphosphatidylethanolamine can be obtained by, for example, carrying out a base exchange reaction of choline and ethanolamine using phospholipase D, with diacylphosphatidylcholine as a raw material. Specifically, a chloroform solution of diacylphosphatidylcholine, and water with phospholipase D and ethanolamine dissolved therein are mixed in an appropriate ratio, whereby a crude reaction product can be obtained. The crude reaction product is purified using a chloroform/methanol/aqueous solvent in a silica gel column, whereby the desired diacylphosphatidylethanolamine can be obtained. Those skilled in the art are able to carry out this process using appropriately chosen column purification conditions such as solvent composition ratio.

As a terminal-modified derivative, a diacylphosphatidylethanolamine terminal-modified derivative prepared by binding one end of a divalent reactive compound to the amino group of diacylphosphatidylethanolamine can be mentioned. As the divalent reactive compound, a compound having at least one end thereof an aldehyde group or succinic imide group capable of reacting with the amino group of diacylphosphatidylethanolamine can be utilized. As divalent reactive compounds having an aldehyde group, glyoxal, glutaraldehyde, succinedialdehyde, terephthalaldehyde and the like can be mentioned. Preferably, glutaraldehyde can be mentioned. As divalent reactive compounds having a succinic imide group, dithiobis(succinimidyl propionate), ethylene glycol-bis(succinimidyl succinate), disuccinimidyl succinate, disuccinimidyl suberate, disuccinimidyl glutarate and the like can be mentioned.

As divalent reactive compounds having a succinimide group at one end thereof and a maleimide group at the other end, N-succinimidyl 4-(p-maleimidophenyl) butyrate, sulfosuccinimidyl-4-(p-maleimidophenyl) butyrate, N-succinimidyl-4-(p-maleimidophenyl) acetate, N-succinimidyl-4-(p-maleimidophenyl) propionate, succinimidyl-4-(N-maleimidoethyl)-cyclohexane-1-carboxylate, sulfosuccinimidyl-4-(N-maleimidoethyl)-cyclohexane-1-carboxylate, N-(γ-maleimidobutyryloxy)succinimide, N-(ε-maleimidocaproyloxy)succinimide and the like can be mentioned. Using these divalent reactive compounds, a diacylphosphatidylethanolamine terminal-modified derivative having a maleimide group as a functional group can be obtained. The functional group at one end of a divalent reactive compound as described above is bound to the amino group of diacylphosphatidylethanolamine, whereby a diacylphosphatidylethanolamine terminal-modified derivative can be obtained.

As an example of a method of binding the peptide to the surface of a liposome, a method can be mentioned wherein a liposome comprising one of the above-described reactive phospholipids is prepared, and then the peptide is added to bind the peptide to the reactive phospholipid in the liposome. Also by binding the peptide to a reactive phospholipid in advance, and then mixing the thus-obtained reactive phospholipid having the peptide bound thereto with a phospholipid other than the reactive phospholipid and a liposome stabilizer, a liposome having the peptide bound to the surface thereof can be obtained. A method of binding the peptide to a reactive phospholipid is well known in the art.

The phospholipid membrane constituting the liposome moiety of the peptide-bound liposome of the present invention comprises at least 1 kind, for example, 2 kinds or more, preferably 3 kinds or more, of phospholipids having an acyl group having 14 to 24 carbon atoms and one unsaturated bond or a hydrocarbon group having 14 to 24 carbon atoms and one unsaturated bond.

For example, the phospholipid membrane constituting the liposome moiety of the peptide-bound liposome of the present invention comprises at least 1 kind, for example, 2 kinds or more, preferably 3 kinds or more, of phospholipids having an acyl group having 14 to 24 carbon atoms and one unsaturated bond or a hydrocarbon group having 14 to 24 carbon atoms and one unsaturated bond, selected from among diacylphosphatidylserine, diacylphosphatidylglycerol, diacylphosphatidic acid, diacylphosphatidylcholine, diacylphosphatidylethanolamine, succinimidyl-diacylphosphatidylethanolamine, and maleimido-diacylphosphatidylethanolamine.

The phospholipid membrane constituting the liposome moiety of the peptide-bound liposome of the present invention preferably comprises at least 1 kind of each of:
an acidic phospholipid containing an acyl group having 14 to 24 carbon atoms and one unsaturated bond or a hydrocarbon group having 14 to 24 carbon atoms and one unsaturated bond,
a neutral phospholipid containing an acyl group having 14 to 24 carbon atoms and one unsaturated bond or a hydrocarbon group having 14 to 24 carbon atoms and one unsaturated bond, and
a reactive phospholipid containing an acyl group having 14 to 24 carbon atoms and one unsaturated bond or a hydrocarbon group having 14 to 24 carbon atoms and one unsaturated bond.

In the present invention, as a liposome stabilizer, sterols or tocopherols can be used. The sterols may be those generally known as sterols; for example, cholesterol, sitosterol, campesterol, stigmasterol, brassica sterol and the like can be mentioned; in view of availability and the like, cholesterol is used particularly preferably. The above-described tocopherols may be those generally known as tocopherols; for example, in view of availability and the like, commercially available α-tocopherol is preferably mentioned.

Furthermore, as far as the effect of the present invention is not affected, the phospholipid membrane constituting the liposome moiety of the peptide-bound liposome of the present invention may comprise a publicly known constituent capable of constituting a liposome.

As an example of the composition of the phospholipid membrane constituting the liposome moiety of the peptide-bound liposome of the present invention, the following can be mentioned:
(A) a phospholipid containing an acyl group having 14 to 24 carbon atoms and one unsaturated bond or a hydrocarbon group having 14 to 24 carbon atoms and one unsaturated bond 1 to 99.8 mol %;
(B) a liposome stabilizer 0.2 to 75 mol %

The content of each component is indicated as mol % to all components of the phospholipid membrane constituting the liposome moiety of the peptide-bound liposome.

The content of the above-described component (A) is, from the viewpoint of liposome stability, preferably 10 to 90 mol %, more preferably 30 to 80 mol %, and still more preferably 50 to 70 mol %.

The content of the above-described component (B) is, from the viewpoint of liposome stability, preferably 5 to 70 mol %, more preferably 10 to 60 mol %, and still more preferably 20 to 50 mol %. If the content of the stabilizer exceeds 75 mol %, the liposome stability is affected, and this is undesirable.

The above-described component (A) includes the following:
(a) a phospholipid containing an acyl group having 14 to 24 carbon atoms and one unsaturated bond or a hydrocarbon group having 14 to 24 carbon atoms and one unsaturated bond, to which the peptide is not bound, and
(b) a phospholipid containing an acyl group having 14 to 24 carbon atoms and one unsaturated bond or a hydrocarbon group having 14 to 24 carbon atoms and one unsaturated bond, to which the peptide is bound.

The content of the above-described component (a) is normally 0.01 to 85 mol %, preferably 0.1 to 80 mol %, more preferably 0.1 to 60 mol %, still more preferably 0.1 to 50 mol %.

The content of the above-described component (b) is normally 0.2 to 80 mol %, preferably 0.3 to 60 mol %, more preferably 0.4 to 50 mol %, and still more preferably 0.5 to 25 mol %. If the content is less than 0.2 mol %, the amount of the peptide of the present invention decreases, so that it becomes difficult to activate cytotoxic T lymphocytes to a practically sufficient level; if the content exceeds 80 mol %, liposome stability decreases.

The phospholipid of the above-described component (a) normally includes the above-described acidic phospholipid and neutral phospholipid. The phospholipid of the above-described component (b) includes the above-described reactive phospholipid.

The content of the acidic phospholipid is normally 1 to 85 mol %, preferably 2 to 80 mol %, more preferably 4 to 60 mol %, and still more preferably 5 to 40 mol %. If the content is less than 1 mol %, the zeta potential decreases and the liposome stability lowers, and it becomes difficult to activate cytotoxic T lymphocytes to a practically sufficient level. Meanwhile, if the content exceeds 85 mol %, the content of the phospholipid with the peptide bound thereto in the liposome decreases, making it difficult to activate cytotoxic T lymphocytes to a practically sufficient level.

The content of the neutral phospholipid is normally 0.01 to 80 mol %, preferably 0.1 to 70 mol %, more preferably 0.1 to 60 mol %, and still more preferably 0.1 to 50 mol %. If the content exceeds 80.0 mol %, the contents of the acidic phospholipid, the phospholipid with the peptide bound thereto and the liposome stabilizer in the liposome decrease, so that it becomes difficult to activate cytotoxic T lymphocytes to a practically sufficient level.

A phospholipid with the peptide bound thereto is obtained by binding the peptide to the reactive phospholipid described above; the ratio of the reactive phospholipid bound to the peptide can be chosen as appropriate, as far as the effect of the present invention is not interfered with, according to the kind of functional group used for the binding, binding treatment conditions employed and the like.

For example, when a terminal-modified derivative of diacylphosphatidylethanolamine obtained by binding one end of disuccinimidyl succinate, a divalent reactive compound, to the terminus amino group of diacylphosphatidylethanolamine, is used as the reactive phospholipid, it is possible to bind 10 to 99% of the reactive phospholipid to the peptide by choosing binding treatment conditions. In this case, the reactive phospholipid not bound to the peptide becomes an acidic phospholipid and gets contained in the liposome.

As a preferred mode of the phospholipid membrane constituting the liposome moiety of the peptide-bound liposome of the present invention, the following composition can be mentioned:
(I) an acidic phospholipid containing an acyl group having 14 to 24 carbon atoms and one unsaturated bond or a hydrocarbon group having 14 to 24 carbon atoms and one unsaturated bond 1 to 85 mol %;
(II) a neutral phospholipid containing an acyl group having 14 to 24 carbon atoms and one unsaturated bond or a hydrocarbon group having 14 to 24 carbon atoms and one unsaturated bond 0.01 to 80 mol %;
(III) a phospholipid containing an acyl group having 14 to 24 carbon atoms and one unsaturated bond or a hydrocarbon group having 14 to 24 carbon atoms and one unsaturated bond, with the peptide bound thereto 0.2 to 80 mol %;
(IV) a liposome stabilizer 0.2 to 75 mol %.
(100 mol % in total)

As a more preferable mode of the phospholipid membrane constituting the liposome moiety of the peptide-bound liposome of the present invention, the following composition can be mentioned:
the above-described component (I) 2 to 80 mol %
the above-described component (II) 0.1 to 70 mol %
the above-described component (III) 0.3 to 60 mol %
the above-described component (IV) 10 to 70 mol %
(100 mol % in total)

As a still more preferable mode of the phospholipid membrane constituting the liposome moiety of the peptide-bound liposome of the present invention, the following composition can be mentioned:
the above-described component (I) 4 to 60 mol %
the above-described component (II) 0.1 to 60 mol %
the above-described component (III) 0.4 to 50 mol %
the above-described component (IV) 20 to 60 mol %
(100 mol % in total)

As a particularly preferable mode of the phospholipid membrane constituting the liposome moiety of the peptide-bound liposome of the present invention, the following composition can be mentioned:
the above-described component (I) 5 to 40 mol %
the above-described component (II) 0.1 to 50 mol %
the above-described component (III) 0.5 to 25 mol %
the above-described component (IV) 25 to 55 mol %
(100 mol % in total)

The peptide-bound liposome of the present invention is characterized in that the unsaturated acyl group or unsaturated hydrocarbon group contained in the phospholipid in the phospholipid membrane constituting the liposome moiety thereof has 14 to 24 carbon atoms; as far as the effect of the present invention is not interfered with, the phospholipid membrane may comprise a phospholipid comprising an unsaturated acyl group or unsaturated hydrocarbon group having a number of carbon atoms less than 14 or exceeding 24. The ratio of the number of unsaturated acyl groups or unsaturated hydrocarbon groups with 14 to 24 carbon atoms, relative to the total number of all unsaturated acyl groups or unsaturated hydrocarbon groups contained in the phospholipid in the phospholipid membrane constituting the liposome moiety of the peptide-bound liposome of the present invention is, for example, 50% or more, preferably 60% or more, more preferably 75% or more, still more preferably 90% or more, and most preferably 97% or more (e.g., substantially 100%).

The phospholipid membrane constituting the liposome moiety of the peptide-bound liposome of the present invention may comprise, as far as the effect of the present invention is not interfered with, a lipid, other than a phospholipid, having an acyl group or hydrocarbon group with 14 to 24 carbon atoms. The content of the lipid is normally 40 mol % or less, preferably 20 mol % or less, more preferably 10 mol % or less, and still more preferably 5 mol % or less (e.g., substantially 0 mol %).

The liposome moiety of the peptide-bound liposome of the present invention can be obtained by a method wherein components (phospholipid, reactive phospholipid, liposome stabilizer, and the peptide and the like) are appropriately blend and processed, and the product is added to an appropriate solvent, or other methods.

For example, methods of production such as the extrusion method, vortex mixer method, sonication method, surfactant removal method, reversed-phase evaporation method, ethanol injection method, pre-vesicle method, French press method, W/O/W emulsion method, annealing method, and freeze-thaw method can be mentioned. The form of liposome is not particularly limited; by choosing one of the aforementioned methods of liposome production as appropriate, liposomes having various sizes and forms such as multilayer liposomes, small monolayer membrane liposomes, and large monolayer membrane liposomes can be produced.

The particle diameter of the liposome is not particularly limited, but in view of storage stability and the like, the particle diameter is 20 to 600 nm, preferably 30 to 500 nm, more preferably 40 to 400 nm, still more preferably 50 to 300 nm, and most preferably 70 to 230 nm.

In the present invention, to improve the physicochemical stability of the liposome, during or after preparing the liposome, a saccharide or a polyhydric alcohol may be added to the internal water phase and/or external water phase of the liposome. In particular, if long storage or storage during formulation is required, it is preferable to add and dissolve a saccharide or polyhydric alcohol as a liposome protector, and to remove water by freeze-drying, to obtain a freeze-dried product of a phospholipid composition.

As examples of the saccharide, monosaccharides such as glucose, galactose, mannose, fructose, inositol, ribose, and xylose; disaccharides such as saccharose, lactose, cellobiose, trehalose, and maltose; trisaccharides such as raffinose and melezitose; oligosaccharides such as cyclodextrin; polysaccharides such as dextrin; sugar alcohols such as xylitol, sorbitol, mannitol, and maltitol, and the like can be mentioned. Of these saccharides, monosaccharides or disaccharides are preferable, and glucose or saccharose is particularly preferable in view of availability and the like.

As examples of the polyhydric alcohol, glycerin compounds such as glycerin, diglycerin, triglycerin, tetraglycerin, pentaglycerin, hexaglycerin, heptaglycerin, octaglycerin, nonaglycerin, decaglycerin, and polyglycerin; sugar alcohol compounds such as sorbitol and mannitol; ethylene glycol, diethylene glycol, triethylene glycol, tetraethylene glycol, pentaethylene glycol, hexaethylene glycol, heptaethylene glycol, octethylene glycol, nonethylene glycol and the like can be mentioned. Thereof, glycerin, diglycerin, triglycerin, sorbitol, mannitol, and polyethylene glycols having molecular weights of 400 to 10,000 are preferable in view of availability.

The concentration of the saccharide or polyhydric alcohol contained in the internal water phase and/or external water phase of the liposome, based on concentration by weight relative to the liposome liquid, is, for example, 1 to 20% by weight, preferably 2 to 10% by weight.

When the peptide-bound liposome of the present invention is produced, it is possible to obtain the peptide-bound liposome of the present invention conveniently by preparing a liposome prior to the binding of the peptide, then binding the peptide.

For example, a suspension of a liposome comprising a phospholipid, a liposome stabilizer, and a reactive phospholipid for binding the peptide to the membrane surface is prepared, and sucrose, one of the aforementioned saccharides, is added to the external water phase thereof at about 2 to 10% by weight, and dissolved. This saccharide-added preparation is transferred to a 10 ml glass vial, placed in a shelf rack type freeze-drier, and cooled to −40° C. and the like to freeze the sample, after which a freeze-dried product is obtained by a conventional method.

The freeze-dried product of the liposome obtained here can be stored for a long time because it is deprived of water; by adding the particular peptide when necessary, and performing the subsequent steps, the completed peptide-bound liposome of the present invention can be obtained conveniently and quickly. If the interaction between the peptide and the liposome is intense and the instability is severe and the like, it is very convenient to preserve the liposome at the stage of a freeze-dried product, as described here, and to bind the peptide when necessary before use.

The phospholipid membrane constituting the liposome moiety of the peptide-bound liposome of the present invention can have a phospholipid with the peptide bound thereto. As methods of obtaining a liposome comprising a phospholipid with the peptide bound thereto, the following methods (A) and (B) can be mentioned.

(A) A method wherein a liposome comprising a phospholipid, a reactive lipid, and a liposome stabilizer is prepared, the peptide and a divalent reactive compound are added thereto, and the functional group of the reactive phospholipid contained in the liposome and the functional group of the peptide are joined via a divalent reactive compound. The divalent reactive compound used here can be the same as that used to prepare a terminal-modified derivative of the reactive phospholipid. Specifically, as divalent reactive compounds having an aldehyde group, glyoxal, glutaraldehyde, succindialdehyde, terephthalaldehyde and the like can be mentioned. Preferably, glutaraldehyde can be mentioned. Furthermore, as divalent reactive compounds having a succinic imide group, dithiobis(succinimidyl propionate), ethylene glycol-bis(succinimidyl succinate), disuccinimidyl succinate, disuccinimidyl suberate, disuccinimidyl glutarate and the like can be mentioned. As divalent reactive compounds having a succinimide group at one end and a maleimide group at the other end, N-succinimidyl-4-(p-maleimidophenyl) butyrate, sulfosuccinimidyl-4-(p-maleimidophenyl) butyrate, N-succinimidyl-4-(p-maleimidophenyl) acetate, N-succinimidyl-4-(p-maleimidophenyl) propionate, succinimidyl-4-(N-maleimidoethyl)-cyclohexane-1-carboxylate, sulfosuccinimidyl-4-(N-maleimidoethyl)-cyclohexane-1-carboxylate, N-(γ-maleimidobutyryloxy)succinimide, N-(ε-maleimidocaproyloxy)succinimide and the like can be used. Using such a divalent reactive compound, a terminal-modified derivative of a reactive phospholipid (e.g., phosphatidylethanolamine) having a maleimide group as a functional group is obtained.

(B) A method wherein a liposome comprising a phospholipid, a reactive phospholipid, and a liposome stabilizer is prepared, the peptide is added thereto, and the functional group of the reactive phospholipid contained in the liposome and the functional group of the peptide are joined and bound.

As examples of the kind of the bond in the foregoing (A) and (B), ionic bonds, hydrophobic bonds, covalent bonds and the like can be mentioned, and the bond is preferably a covalent bond. Furthermore, as specific examples of the covalent bond, a Schiff's base bond, an amide bond, a thioether bond, an ester bond and the like can be mentioned.

These two methods both enable the binding of the peptide to the reactive phospholipid contained in the phospholipid membrane constituting the liposome, resulting in the formation of a phospholipid having the peptide bound thereto in the liposome.

As a specific example of a method of binding the raw material liposome and the peptide via a divalent reactive compound, in the aforementioned method (A), a method with the use of a Schiff's base bond can be mentioned. As a method of binding a liposome and the peptide via a Schiff's base bond, a method can be mentioned wherein a liposome having an amino group on the surface thereof is prepared, the peptide is added to a suspension of the liposome, then a dialdehyde is added as a divalent reactive compound, and the amino group on the liposome surface and the amino group in the peptide are bound via a Schiff's base.

As a specific example of this binding procedure, the following method can be mentioned.
(A-1) To obtain a liposome having an amino group on the surface thereof, a reactive phospholipid containing an acyl group having 14 to 24 carbon atoms and one unsaturated bond or a hydrocarbon group having 14 to 24 carbon atoms and one unsaturated bond (e.g., phosphatidylethanolamine) is mixed in a liposome raw material lipid (phospholipid, liposome stabilizer and the like) to prepare a liposome wherein a specified amount of amino groups is present on the liposome surface.
(A-2) The peptide is added to the liposome suspension.
(A-3) Next, glutaraldehyde, as a divalent reactive compound, is added, and the reaction is allowed to proceed for a specified time to form a Schiff's base bond between the liposome and the peptide.
(A-4) Thereafter, to inactivate the reactivity of excess glutaraldehyde, glycine, as a water-soluble compound containing an amino group, is added to the liposome suspension to cause the reaction.
(A-5) The portion of the peptide not bound to the liposome, the reaction product of glutaraldehyde and glycine, and excess glycine are removed by a method such as gel filtration, dialysis, ultrafiltration or centrifugation, to yield a suspension of the peptide-bound liposome of the present invention.

As a specific example of the method (B) above, a method can be mentioned wherein a reactive phospholipid having a functional group capable of forming an amide bond, a thioether bond, a Schiff's base bond, an ester bond and the like is introduced into the phospholipid membrane constituting the liposome. As specific examples of the functional group, a succinimide group, a maleimide group, an amino group, an imino group, a carboxyl group, a hydroxy group, a thiol group and the like can be mentioned.

As an example of the reactive phospholipid to be introduced into the phospholipid membrane constituting the liposome, the aforementioned terminal-modified derivative of a reactive phospholipid, modified at the amino group end thereof, having an acyl group having 14 to 24 carbon atoms and one unsaturated bond or a hydrocarbon group having 14 to 24 carbon atoms and one unsaturated bond (e.g., phosphatidylethanolamine) can be used.

Specific examples of this binding procedure are hereinafter described with reference to a case wherein diacylphosphatidylethanolamine is used.
(B-1) A diacylphosphatidylethanolamine having an acyl group having 14 to 24 carbon atoms and one unsaturated bond and disuccinimidyl succinate are reacted only at one end by a known method to yield a disuccinimidyl succinate-bound diacylphosphatidylethanolamine having a succinimide group as a functional group at the end.
(B-2) The aforementioned disuccinimidyl succinate-bound diacylphosphatidylethanolamine and other liposome components (phospholipid, liposome stabilizer and the like) are mixed by a publicly known method to prepare a liposome having a succinimide group as a functional group on the surface thereof.
(B-3) The peptide is added to the aforementioned liposome suspension to allow the amino group in the peptide and the succinimide group on the liposome surface to react with each other.
(B-4) The unreacted portion of the peptide, reaction byproducts and the like are removed by a method such as gel filtration, dialysis, ultrafiltration and centrifugation to yield a suspension of a liposome comprising a phospholipid with the peptide of the present invention bound thereto.

When the liposome and the peptide are bound, it is practically preferable that an amino group or a thiol group, which are often contained as a functional group, be the subject. When an amino group is the subject, a Schiff's base bond can be formed by reacting with a succinimide group. When a thiol group is the subject, a thioether bond can be formed by reacting with a maleimide group.

2. Peptide

The present invention also provides a peptide comprising an amino acid sequence shown by SEQ ID NO: 1 or 2, having a length of 9-11 amino acids, and capable of inducing cytotoxic T lymphocyte (peptide of the present invention).

The peptide of the present invention is a peptide per se consisting of a superior epitope sequence shown by SEQ ID NO: 1 or 2, or a peptide produced by intracellular cleavage by the action of proteasome and the like. Therefore, the peptide of the present invention has superior property substantially the same as that of the peptide consisting of the epitope sequence shown by SEQ ID NO: 1 or 2. That is, the peptide of the present invention can induce cytotoxic T lymphocytes. When the peptide of the present invention is applied to the production of the following cytotoxic T lymphocyte activator or hepatitis C virus vaccine of the present invention, it shows a superior effect in killing the cells infected with hepatitis C virus or preventing infection with hepatitis C virus.

While the length of the peptide of the present invention is not particularly limited, it is generally 9-11 amino acids, preferably 9-10 amino acids, more preferably 9 amino acids. When the length of the peptide of the present invention is not less than 10 amino acids, the peptide of the present invention has an addition sequence on the N-terminus side and/or C-terminus side of the epitope sequence shown by SEQ ID NO: 1 or 2. The length and amino acid sequence of the addition sequence is not particularly limited as long as the above-mentioned property of the peptide of the present invention is not impaired. For example, the addition sequence may be an amino acid sequence actually present in adjacency to the partial sequence corresponding to SEQ ID NO: 1 or 2, in the amino acid sequence of NS3 protein of hepatitis C virus. In addition, the addition sequence is particularly preferably a residue capable of overcoming the selection of presented antigen due to individual differences (polymorphism) of MHC, during intracellular formation of major histocompatibility complex (MHC) by the above-mentioned peptide.

The peptide of the present invention can be prepared by a method similar to that for a peptide contained in the above-mentioned peptide-bound liposome of the present invention.

3. Use of the Peptide and Peptide-Bound Liposome of the Present Invention

Using the peptide or peptide-bound liposome of the present invention, it is possible to potently induce cytotoxic T lymphocytes (CTL) that recognize the peptide of the present invention or the epitope peptide of the present invention in a specific manner. The cytotoxic T lymphocytes induced by the peptide or peptide-bound liposome of the present invention kill the cells presenting the peptide of the present invention or the epitope peptide of the present invention onto HLA as a result of infection with hepatitis C virus, and eliminate these cells. Therefore, the peptide and peptide-bound liposome of the present invention are useful as a cytotoxic T lymphocyte activator or hepatitis C virus vaccine for the treatment or prophylaxis of hepatitis C.

When the peptide or peptide-bound liposome of the present invention is used as a cytotoxic T lymphocyte activator or hepatitis C virus vaccine, it can be prepared as a preparation according to a conventional method. The peptide or peptide-bound liposome of the present invention is of low toxicity, and can be administered orally or parenterally (e.g., intravascular administration, subcutaneous administration and the like) as a liquid as it is, or as a pharmaceutical composition in an appropriate dosage form, to humans, non-human mammals (e.g., rats, rabbits, sheep, pigs, cattle, cats, dogs, monkeys and the like), birds (chicken, geese, domestic ducks, ostriches, quails and the like). The animal being the subject of administration of the peptide or peptide-bound liposome of the present invention is normally a mammal (e.g., human) or bird which can be infected with the target hepatitis C virus. The peptide or peptide-bound liposome of the present invention is normally administered parenterally.

The cytotoxic T lymphocyte activator and hepatitis C virus vaccine of the present invention may be administered as an active ingredient peptide or peptide-bound liposome as it is, or may be administered as an appropriate pharmaceutical composition. The pharmaceutical composition used for the administration may comprise the above-described peptide or peptide-bound liposome and a pharmacologically acceptable carrier, diluent or excipient. Such a pharmaceutical composition is provided as a dosage form suitable for oral or parenteral administration.

As examples of the composition for parenteral administration, injections, suppositories and the like are used; the injections may include dosage forms such as intravenous injections, subcutaneous injections, intracutaneous injections, intramuscular injections, and drip infusion injections. Such an injection can be prepared according to a known method. The injection can be prepared by, for example, dissolving or suspending the above-described peptide or peptide-bound liposome in a sterile aqueous solvent normally used for injections. As examples of the aqueous solvent for injection, distilled water; physiological saline; buffer solutions such as phosphate buffer solution, carbonate buffer solution, tris buffer solution, and acetate buffer solution, and the like can be used. The pH of the aqueous solvent is 5 to 10, preferably 6 to 8. The prepared injection liquid is preferably filled in an appropriate ampoule.

Also, by subjecting a solution of the peptide of the present invention or a suspension of the peptide-bound liposome of the present invention to a treatment such as vacuum drying and freeze-drying, a powder preparation of the peptide of the present invention or the peptide-bound liposome of the present invention can also be prepared. The peptide of the present invention or the peptide-bound liposome of the present invention can be preserved in a powder state, and can be supplied for use by dispersing the powder in an aqueous solvent for injection freshly before use.

The cytotoxic T lymphocyte activator and hepatitis C virus vaccine of the present invention, to enhance the effect thereof, may further comprise an adjuvant. As the adjuvant, aluminum hydroxide gel, Freund's complete adjuvant, Freund's incomplete adjuvant, *Bordetella pertussis* adjuvant, poly (I,C), CpG-DNA and the like can be mentioned, and CpG-DNA is particularly preferable. CpG-DNA, a DNA comprising the bacterial non-methylated CpG motif, is known to work as a ligand for a particular receptor (Toll-like receptor 9) (for details, see Biochim. Biophys. Acta 1489, 107-116 (1999) and Curr. Opin. Microbiol. 6, 472-477 (2003)). CpG-DNA is capable of enhancing the induction of cytotoxic T lymphocytes by the peptide or peptide-bound liposome of the present invention, by activating dendritic cells (DC).

The content of an active ingredient (the peptide or peptide-bound liposome of the present invention) in the pharmaceutical composition is normally about 0.1 to 100% by weight, preferably about 1 to 99% by weight, and still more preferably about 10 to 90% by weight, relative to the entire pharmaceutical composition.

If the cytotoxic T lymphocyte activator or hepatitis C virus vaccine of the present invention comprises an adjuvant, the content of the adjuvant (e.g., CpG-DNA) can be set as appropriate, as far as the induction of cytotoxic T lymphocytes can be enhanced, and the content is normally about 0.01 to 10% by weight, preferably about 0.1 to 5% by weight, relative to the entire pharmaceutical composition.

The dose of the peptide of the present invention or the peptide-bound liposome of the present invention varies depending on the subject of administration, method of administration, dosage form and the like; for example, in the case of activation of cytotoxic T lymphocytes in a living organism by subcutaneous administration or nasal administration, the dose is given normally in the range of 1 μg to 1000 μg, preferably 20 μg to 100 μg, based on the peptide of the present invention, per administration, for each adult (weighing 60 kg), normally for 4 weeks to 18 months, 2 to 3 times. When hepatitis C virus infection is prevented by subcutaneous administration, the dose is given normally in the range of 1 μg to 1000 μg, preferably 20 μg to 100 μg, based on the peptide of the present invention, per administration, generally for 4 weeks to 18 months, 2 times to 3 times. Furthermore, when hepatitis C is treated by subcutaneous administration, the dose is in the range of 1 μg to 1000 μg, preferably 20 μg to 100 μg, based on the peptide of the present invention, per administration, generally for 4 weeks to 18 months, 2 times to 3 times.

The present invention is explained in more detail in the following by referring to Examples, which are not to be construed as limitative.

EXAMPLES

Immunization of Mouse

As the mouse, HHD mouse wherein H-2D and H-2K, which are mouse-inherent MHC class I genes, and β2-microglobulin gene were knocked out, and human HLA-A*0201 and β2-microglobulin genes were introduced and expressed (Pascolo S, Bervas N, Ure J M, Smith A G, Lemonnier F A, Perarnau B. The Journal of Experimental Medicine 1997; 185(12):2043-2051) was used. For a part of the experiment, an offspring (F1) generated by crossbreeding HHD (male) and C57BL/6 mouse (female, purchased from Tokyo Laboratory Animal Science Co., Ltd.) was used. For immunization with peptide-bound liposome, a liposome bound with a pool of 6 kinds of peptides was subcutaneously injected at 100 μl/mouse and a liposome bound with a single peptide was subcutaneously injected at 20 μl/mouse, each together with CpG5002 (synthesis was entrusted to Hokkaido System Science Co., Ltd., 5 μg/mouse), and 7 days later, the mice were subjected to (1) infection experiment with recombinant vaccinia virus that expresses NS3 (VV-NS3), (2) $^{51}$Cr release test or (3) ELISPOT (IFN-γ).

As positive control of immunization, a mouse intraperitoneally inoculated with 5×10$^7$ PFU of recombinant adenovirus Adex1CA3269 that expresses NS3, NS4 and NS5A genes of HCV (Makimura M, Miyake S, Akino N et al. Vaccine 1996; 14:28-34, Urbani S, Uggeri J, Matsuura Y et al. Hepatology 2001; 33(6):1533-1543, Ohno S, Moriya O, Yoshimoto T, Hayashi H, Akatsuka T, Matsui M., Viral Immunol. 2006; 19:458-467) was used. In a comparative test of epitope immunogenicity, immunization by intraperitoneal inoculation of 1×10$^7$ PFU of recombinant vaccinia virus that expresses HCV-NS3 gene (VV-NS3) was also performed in addition to the above-mentioned immunization with Adex1CA3269.

(Vaccinia Virus Infection Experiment)

The recombinant vaccinia virus that expresses HCV-NS3 gene (VV-NS3) was prepared as follows in the same manner as in the method already reported (Ohnishi Y, Shioda T, Nakayama K et al. The Journal of Virology 1994; 68(6): 4075-4079). Using HCV cDNA clone pBRTM/HCV1-3011con (Kolykhalov A A, Agapov E V, Blight K J, Mihalik K, Feinstone S M, Rice C M. Science 1997; 277: 570-574) as a template, the HCV-NS3 gene was amplified using sense primer 5'-GCCGGATCCATGGTCTCCAAGGGGTGGAG-3' (SEQ ID NO: 29) and antisense primer 5'-TCACGTGAC-GACCTCCAGGTCGGCC-3' (SEQ ID NO: 30), and integrated into a transfer vector pNZ68K2. A vaccinia virus integrated with the HCV-NS3 gene (VV-NS3) was prepared by homologous recombination of the transfer vector and wild-type vaccinia virus A (VV-wt) (WR strain), and C143 cell was infected therewith in the presence of 5-bromo-2-deoxyuridine. Plaque purification was repeated three times, and the virus was amplified with CV-1 cell.

The recombinant vaccinia virus (VV-NS3) was intraperitoneally inoculated at 2×10$^6$ PFU to the immunized mouse and, 5 days later, the both ovaries were isolated. The ovaries were homogenized, and the homogenate was diluted with PBS (0.5 ml) containing 1% FCS and 1 mM MgCl$_2$, repeatedly freeze-thawed three times, and sonicated. The homogenate was 10-fold diluted serially, each was added to BS-C-1 cells in a 6-well plate, stained with 0.1% crystal violet 48 hr later, and the plaques were counted. The results are shown by plaque forming unit (PFU) per mouse.

($^{51}$Cr Release Test)

Splenocytes were taken from normal HHD mouse, peptide (10 μm) was added thereto and the mixture was cultured for 2 hr. Thereafter, the cells were exposed to X-ray (40 Gy) irradiation, and washed with a culture medium to give cells for stimulation. Thereto was added 2-fold amount of splenocytes derived from the immunized mouse, and the mixture was cultured for stimulation for 6-7 days. Using same as an effector cell, the cytotoxic activity thereof was measured by a standard $^{51}$Cr release test (Shirai M, Akatsuka T, Pendleton C D et al. J Virol 1992; 66:4098-4106) as follows. As a target cell, used was RMA-HHD (H-2b), which is a cell line derived from the lymphoma of a mouse wherein, like HHD mouse, human HLA-A*0201 and β2-microglobulin genes were introduced and expressed (Pascolo S, Bervas N, Ure J M, Smith A G, Lemonnier F A, Perarnau B. The Journal of Experimental Medicine 1997; 185(12): 2043-2051) (cultured in RPMI1640, 10% FCS and G418 500 μg/ml). To the cells (1×10$^6$ cells) was added 10 μM peptide, and the mixture was cultured for 2 hr. 100 μCi Na$_2$$^{51}$CrO$_4$ was added and the mixture was incubated for 30 min for labeling, washed with a culture medium, and added to a 96-well culture plate at 5×10$^3$ cells/well. The above-mentioned effector cell was added thereto at various effector/target cell ratios (E/T ratio), and the mixture was incubated at 37° C. for 4 hr. The radioactivity in the supernatant was measured by a gamma counter, and "% Specific Lysis" was calculated by the following calculation formula.

$$\% \text{ specific lysis} = [(cpm_{sample} - cpm_{spontaneous})/(cpm_{maximum} - cpm_{spontaneous})] \times 100$$

wherein cpm is a count per minute, spontaneous release is a count in the absence of effector cell, and maximum release is a count on complete lysis of the target cell by the addition of 2% Nonidet P-40.

(ELISPOT (IFN-γ))

T cells that produce interferon gamma (IFN-γ) antigen-specifically in the spleen of the immunized mouse were measured using an ELISPOT kit (BD Bioscience). An anti-IFN-γ antibody (clone R4-6A2, 0.5 μg) was placed in a 96-well plate, the plate was left standing at 4° C. overnight and washed. RPMI 1640 medium containing 10% FCS was added and blocking was performed at room temperature for 2 hr. The splenocytes (1×10$^5$ or 1×10$^6$ cells) of the immunized mouse and spleen cells of normal HHD mouse pulsed with peptide and exposed to X-ray (40 Gy) irradiation in an amount of $^1/_{10}$ thereof was added to each well, and the mixture was cultured at 37° C. for 2 days. The cells of each well were removed by washing, and the well was reacted with biotin-labeled anti-mouse IFN-γ antibody at room temperature for 2 hr, and then with streptavidin-horseradish peroxidase at room temperature for 1 hr. Finally, a substrate solution containing 3-amino-9-ethylcarbazole was added to allow color development of the spots. After drying, the number of the spots in each well was observed and counted under a stereomicroscope.

Reference Example 1

Preparation of Liposome

1) Preparation of Mixed Lipid Powder

Synthesis of a reactive phospholipid consisting of terminal-modified phosphatidylethanolamine (succinimidyl group-dioleoylphosphatidylethanolamine)

2 g of dioleoylphosphatidylethanolamine and 180 μl of triethylamine were added to, and dissolved in, 50 ml of chloroform, and this solution was placed in a 300 ml capacity four-mouthed flask. While stirring this flask with a magnetic stirrer at room temperature, a separately prepared solution of 3 g of disuccinimidyl suberate being a divalent reactive compound in 80 ml of chloroform was added drop by drop over 4 hours according to a conventional method, to allow one end of the disuccinimidyl suberate to react to the amino group of the dioleoylphosphatidylethanolamine. This crude reaction solution was transferred to an eggplant type flask, and the solvent was distilled off using an evaporator. Next, a small amount of chloroform sufficient to dissolve the crude reaction product was added to this flask to obtain a high-concentration crude reaction product solution, and column chromatography was performed using a silica gel, previously equilibrated with chloroform/methanol/water (65/25/1, ratio by volume), according to a conventional method; only the desired fraction wherein one end of the disuccinimidyl suberate is bound to the amino group of the dioleoylphosphatidylethanolamine was recovered, and the solvent was distilled off to yield succinimide group-dioleoylphosphatidylethanolamine being the desired reactive phospholipid.

2) Preparation of Mixed Lipid Powder 1.3354 g (1.6987 mmol) of dioleoylphosphatidylcholine, 0.2886 g (0.2831 mmol) of the succinimide group-dioleoylphosphatidylethanolamine prepared in the foregoing section, 0.7663 g (1.9818 mmol) of cholesterol and 0.4513 g (0.5662 mmol) of sodium dioleoylphosphatidylglycerol were taken in an eggplant type flask, 50 ml of a mixed solvent of chloroform/methanol/water (65/25/4, ratio by volume) was placed therein, and the contents were dissolved at 40° C. Next, the solvent was distilled off under reduced pressure using a rotary evaporator to yield a lipid film. Furthermore, 30 ml of distilled water for injection was added, and this was followed by stirring to yield a homogeneous slurry. This slurry was frozen, and dried in a freeze-drier for 24 hours to yield a mixed lipid powder.

3) Preparation of Liposome

Next, 60 ml of a separately prepared buffer solution (1.0 mM $Na_2HPO_4/KH_2PO_4$, 0.25 M saccharose, pH 7.4, hereinafter abbreviated as buffer solution) was placed in an eggplant type flask containing the above-described mixed lipid powder, and the lipid was hydrated with stirring at 40° C., to yield a liposome. Next, using an extruder, the particle diameter of the liposome was adjusted. First, the liposome was passed through an 8 μm polycarbonate filter, and subsequently through μm, 3 μm, 1 μm, 0.65 μm, 0.4 μm and 0.2 μm filters in this order. Liposome particles having a mean particle diameter of 206 nm (measured by the dynamic light scattering method) were obtained.

Example 1

Search for CTL Epitope 25 kinds of epitopes including 6 kinds reported as CTL epitopes were selected from the amino acid sequence of NS3 region of hepatitis C virus HCV-1a strain polyprotein (GenBank accession#: AAB66324). The predicted antigenicity scores of these epitopes to cytotoxic T cells (CTL) were calculated using a prediction program available on the internet (BIMAS and SYFPEITHI) (Table 1).

TABLE 1

| SEQ name | Position | Sequence | SEQ ID NO | BIMAS | SYFPEITHI | Report | Pool |
|---|---|---|---|---|---|---|---|
| #1 | 1288 | Gly Ser Pro Ile Thr Tyr Ser Thr Tyr | 7 | 82.5 | 28 | + | I |
| #2 | 1627 | Arg Leu Gly Ala Val Gln Asn Glu Val | 8 | 69.6 | 23 |  | II |
| #3 | 1542 | Tyr Met Asn Thr Pro Gly Leu Pro Val | 1 | 231.1 | 23 |  | II |
| #4 | 1131 | Tyr Leu Val Thr Arg His Ala Asp Val | 9 | 319.9 | 24 | + | I |
| #5 | 1547 | Gly Leu Pro Val Cys Gln Asp His Leu | 10 | 10.5 | 21 |  | II |
| #6 | 1313 | Ile Ile Cys Asp Glu Cys His Ser Thr | 11 | 7.1 | 18 |  | I |
| #7 | 1617 | Thr Leu His Gly Pro Thr Pro Leu Leu | 12 | 21.4 | 26 | + | I |
| #8 | 1606 | Gln Met Trp Lys Cys Leu Ile Arg Leu | 13 | 294.5 | 23 |  | II |
| #9 | 1464 | Phe Ser Leu Asp Pro Thr Phe Thr Ile | 14 | 27.6 | 17 |  | III |
| #10 | 1610 | Cys Leu Ile Arg Leu Lys Pro Thr Leu | 15 | 21.4 | 26 |  | II |
| #11 | 1253 | Val Leu Asn Pro Ser Val Ala Ala Thr | 16 | 29.1 | 25 |  | III |
| #12 | 1450 | Ser Val Ile Asp Cys Asn Thr Cys Val | 17 | 25.0 | 19 |  | III |
| #13 | 1510 | Gly Met Phe Asp Ser Ser Val Leu Cys | 5 | 54.4 | 13 |  | III |
| #14 | 1420 | Gly Leu Asp Val Ser Val Ile Pro Thr | 18 | 6.9 | 19 |  | III |
| #15 | 1560 | Gly Val Phe Thr Gly Leu Thr His Ile | 19 | 7.8 | 20 |  | III |
| #16 | 1250 | Lys Val Leu Val Leu Asn Pro Ser Val | 20 | 78.8 | 21 |  | IV |
| #17 | 1648 | cys Met Ser Ala Asp Leu Glu Val Val | 21 | 23.2 | 22 |  | IV |
| #18 | 1178 | Gly Leu Phe Arg Ala Ala Val Cys Thr | 22 | 27.6 | 18 |  | IV |
| #19 | 1645 | Ile Met Thr Cys Met Ser Ala Asp Leu | 3 | 26.2 | 21 |  | IV |
| #20 | 1406 | Lys Leu Val Ala Leu Gly Ile Asn Ala | 23 | 17.4 | 16 | + | I |
| #21 | 1169 | Leu Leu Cys Pro Ala Gly His Ala Val | 24 | 118.2 | 26 | + | I |

TABLE 1-continued

| SEQ name | Position | Sequence | SEQ ID NO | BIMAS | SYFPEITHI | Report | Pool |
|---|---|---|---|---|---|---|---|
| #22 | 1342 | Arg Leu Val Val Leu Ala Thr Ala Thr | 25 | 7.5 | 16 | | insoluble |
| #23 | 1069 | Phe Leu Ala Thr Cys Ile Asn Gly Val | 26 | 735.9 | 29 | | IV |
| #24 | 1176 | Ala Val gly Leu Phe Arg Ala Ala Val | 27 | 23.1 | 20 | | IV |
| #25 | 1039 | Leu Leu Gly Cys Ile Ile Thr Ser Leu | 28 | 83.5 | 28 | + | I |

Example 2

Screening for Peptide Having Vaccine Effect

1) Preparation of Liposome Preparation from Peptide Pool

Of the 25 candidate peptides of Example 1, 24 peptides except #22 with extremely low solubility were pooled in 4 groups (NS3-I to IV). Known 6 CTL epitope peptides were pooled in NS3-I. Using each pool, peptide-bound liposomes were prepared according to the following method.

The liposome (1.5 ml) of Reference Example 1 (preparation of liposome) was placed in a test tube, each peptide pool solution (3 ml) prepared separately was added, and the mixture was reacted by gently stirring at 5° C. for 48 hr. This reaction mixture was applied to gel filtration according to a conventional method using Sepharose CL-4B equilibrated with a buffer. While the object fraction can be easily confirmed since the liposome fraction becomes cloudy, it may be confirmed by an UV detector and the like.

The concentration of phosphorus in the obtained liposome suspension was measured (Phospholipid Test Wako), and the concentration was adjusted by diluting with a buffer such that the phosphorus concentration derived from the phospholipid was 2 mM, whereby each peptide-bound liposome suspension was obtained.

2) Measurement of Vaccine Effect

The peptide-bound liposomes prepared in 1) were measured for the vaccine effect on recombinant vaccinia virus integrated with HCV NS3 (FIG. 1). As a result, each pool showed a certain level of vaccine effect, and NS3-II and NS3-III showed particularly high vaccine effect.

Figure 2:
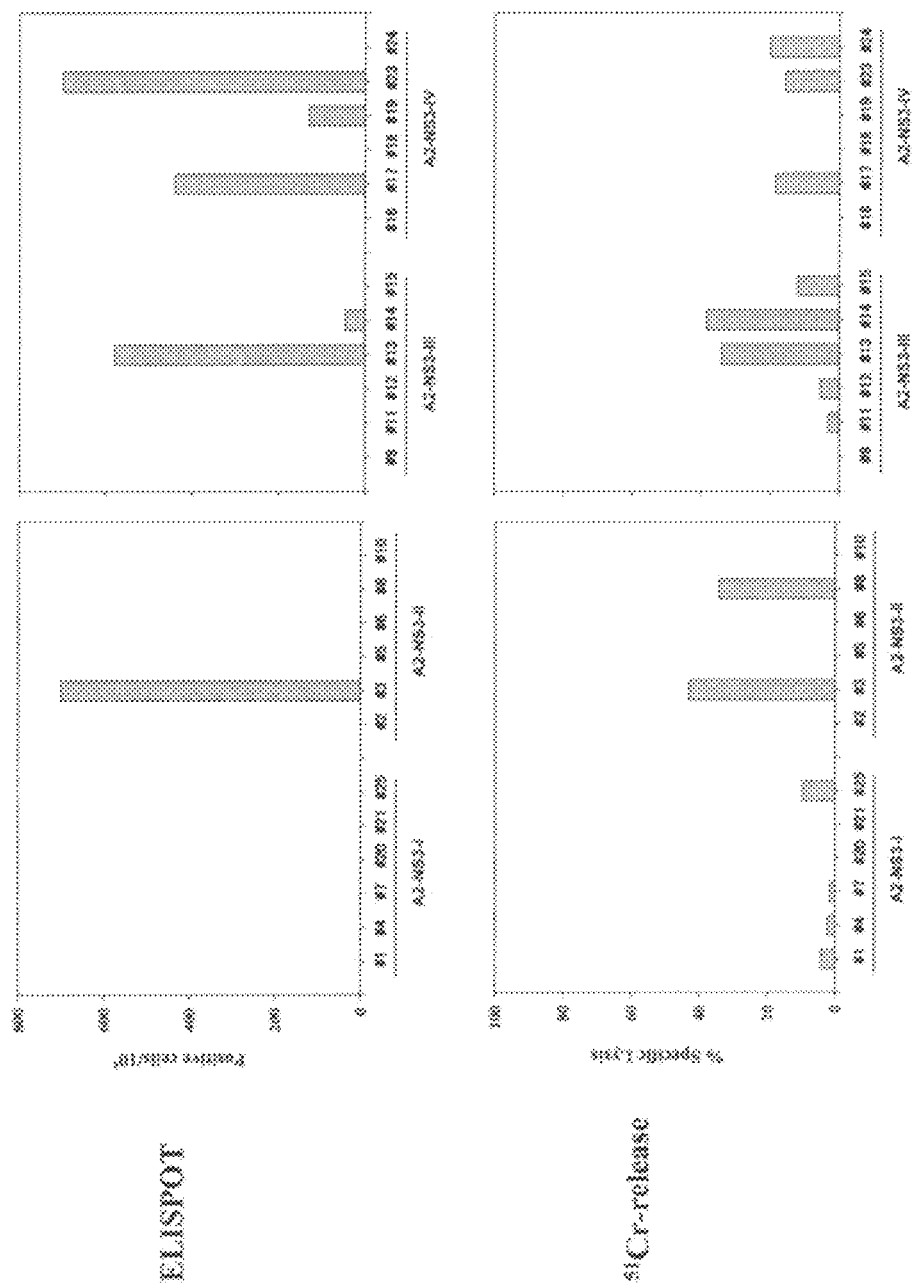
FIG. 2 shows the results of immunogenicity of each peptide in each pool in FIG. 1. The number of IFN-γ productive cells in the stimulation with each peptide was measured by the ELISPOT method. The cytotoxicity of cytotoxic T lymphocyte to the target cell that presents each peptide as an antigen was measured by $^{51}Cr$ release method.

In addition, the immunogenicity of peptide in each pool was measured (FIG. 2). The number of the IFN-γ productive cells due to the stimulation with each peptide was measured by the ELISPOT method, and IFN-γ production due to the stimulation with peptides #3, #13, #14, #17, #19 and #23 was confirmed. In addition, the CTL cytotoxicity was measured by a $^{51}$-Cr release test. As a result, plural peptides including the aforementioned peptides were confirmed to show cytotoxicity. In particular, peptides #3, #8, #13, #14, #17, #19 and #23 strongly induced antigen-specific CTL.

3) Preparation of Liposome Preparation from Each Peptide

Peptide-bound liposomes were prepared from each of the peptides #3, #13, #14, #17, #19 and #23, which suggested CTL inducibility in the above-mentioned test, according to the following method.

1.5 ml of the liposome of Reference Example 1 (Preparation of liposome) was taken in a test tube, 3 ml of a separately prepared solution of each peptide (1.25 mM, solution of a buffer solution) was added, and thereafter the solution was gently stirred at 5° C. for 48 hours to allow the reaction. This reaction liquid was subjected to gel filtration by a conventional method using Sepharose CL-4B, previously equilibrated with the buffer solution.

The phosphorus concentration in the obtained liposome suspension was measured (Phospholipid Test Wako), and the concentration was adjusted by diluting with a buffer such that the phosphorus concentration derived from the phospholipid was 2 mM, whereby each peptide-bound liposome suspension was obtained.

4) Measurement of Vaccine Effect of Peptide-Bound Liposome

The immunogenicity of the peptide-bound liposomes prepared in 3) was measured (FIG. 3). As a result, IFN-γ production was observed by the use of any peptide-bound liposome, which was particularly remarkable when peptide #3 was used. In addition, induction of cytotoxic T cells was also confirmed with peptides #3, #13, #17 and #23. The effect of induction of cytotoxic T cells was also remarkable when peptide #3 was used.

Furthermore, the vaccine effect of these peptide-bound liposomes was examined. As a result, it was clarified that a remarkable vaccine effect can be obtained by using peptides #3, #13 and #19 (FIG. 4).

Peptide #3 is a peptide consisting of the amino acid sequence shown by SEQ ID NO: 1 (YMNTPGLPV), peptide #13 is a peptide consisting of the amino acid sequence shown by SEQ ID NO: 5 (GMFDSSVLC), and peptide #19 is a peptide consisting of the amino acid sequence shown by SEQ ID NO: 3 (IMTCMSADL). These test results suggest the following.

The predicted antigenicity score to cytotoxic T cells (CTL) in the prediction program (BIMAS, SYFPEITHI) is not necessarily correlated with CTL induction activity of peptide-bound liposome.

The CTL induction activity of peptide without binding to liposome is not necessarily correlated with the CTL induction activity of the peptide bound to liposome.

Example 3

Immunogenicity of Peptide #3 in Various Experiment Systems

Figure 5:
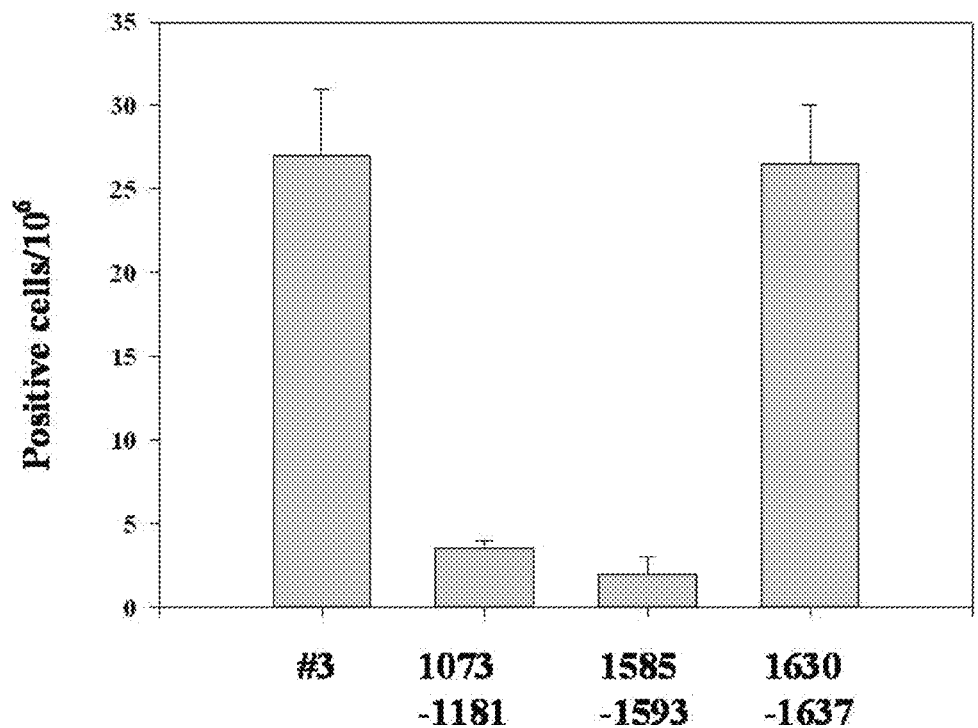
FIG. 5 shows the results of the immunogenicity of liposome-bound peptide#3 examined by ELISPOT. The mouse H-2b epitope peptide 1630-1637-bound liposome showed high immunogenicity, but human HLA-A*0201 epitope 1073-1081 or 1585-1593-bound liposome showed low immunogenicity. In contrast, peptide#3 showed high immunogenicity of the same level as that of mouse epitope 1630-1637 due to the liposome binding.
Figure 6:
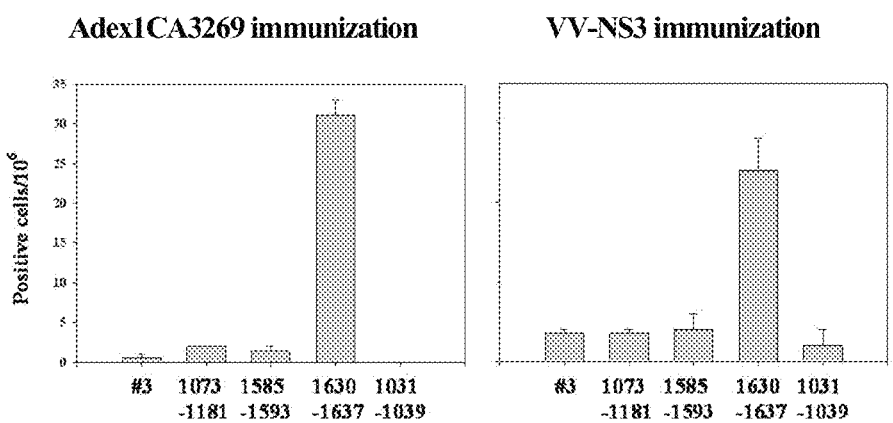
FIG. 6 shows that the immunogenicity of peptide#3 is low in an immunization experiment using two kinds of recombinant viruses Adex1CA3269 and VV-NS3. That is, while peptide#3 does not show immunogenicity when immunized with whole NS3, it shows superior immunogenicity by liposome binding.

The immunogenicity of peptide #3 that showed a remarkable vaccine effect in the above-mentioned test using liposome was further studied using other experiment systems (FIG. 5 and FIG. 6).

As mentioned above, a peptide that induces cytotoxic T lymphocyte by itself does not always efficiently induce cytotoxic T lymphocyte by binding to a liposome. To further confirm this, a mouse that expresses both human HLA-A*0201 gene and mouse-inherent H-2b gene (which is an offspring generated by mating HHD (male) and a C57BL/6 mouse (female)) was immunized with 4 kinds of peptide-bound liposomes, and the immunogenicity thereof was compared (FIG. 5).

As a result, while the liposome bound with epitope peptide 1630-1637 of mouse H-2b showed high immunogenicity, the liposome bound with epitope 1073-1081 or 1585-1593 of human HLA-A*0201 showed low immunogenicity. While the epitope 1073-1081 and epitope 1585-1593 are peptides known as superior epitope peptides of hepatitis C virus, they did not show remarkable immunogenicity. This means that a peptide-bound liposome showing superior immunogenicity cannot always be obtained even when a superior epitope peptide is used. In contrast, peptide #3 showed high immunogenicity of the same level as mouse epitope 1630-1637 due to the liposome binding.

Furthermore, an immunization experiment using Adex13269 and VV-NS3 has clarified that peptide #3 shows low immunogenicity (FIG. 6). The 1031-1039 is HLA-A24 (A*2402) epitope of HCV NS3, which was used as negative control here.

These results demonstrate that peptide #3 does not show immunogenicity when it is immunized with whole NS3, but expresses superior immunogenicity when bound with a liposome. That is, peptide #3 is particularly suitable for use as a cytotoxic T lymphocyte activator or hepatitis C virus vaccine by binding to a liposome.

Example 4

Boost Effect of Lip-#3

Figure 7:
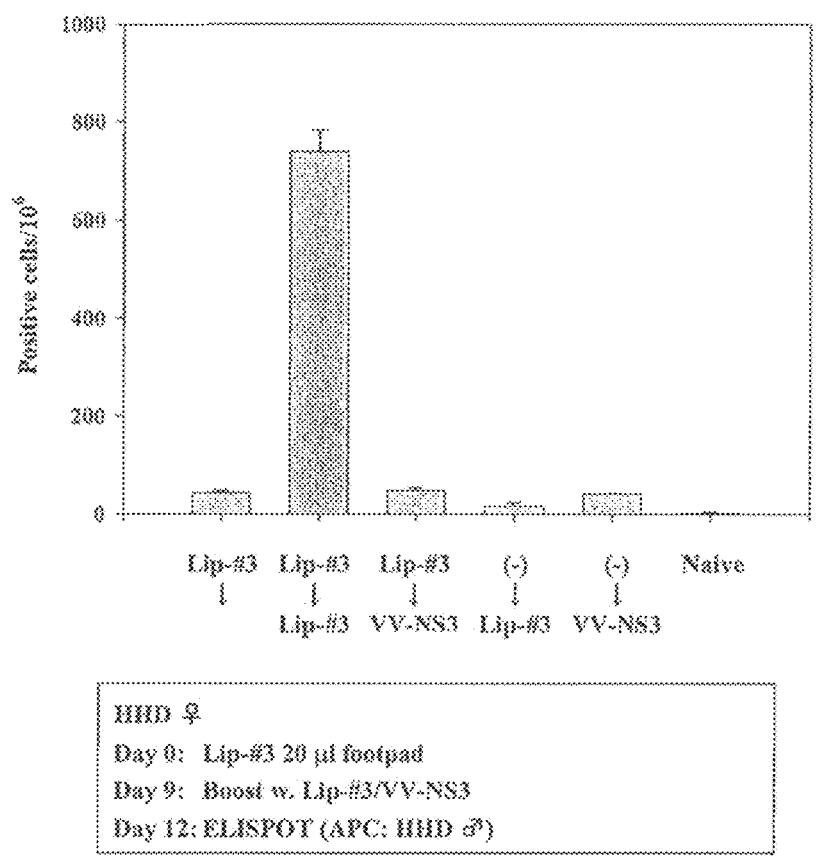
FIG. 7 shows the boost effect of peptide-bound liposome (Lip-#3) prepared from peptide#3. Like the results of FIG. 6, immunogenicity of peptide#3 is not exhibited by immunization with recombinant virus VV-NS3, and a boost effect is also absent.

The boost effect of Lip-#3 was confirmed by ELISPOT (FIG. 7). When Lip-#3 was inoculated twice to an HHD mouse in the time schedule shown in the lower panel of FIG. 7, a remarkable increase of IFN-γ production was observed. This means that Lip-#3 can be used as a vaccine for the treatment of hepatitis C.

Example 5

Dose Dependency of Immunogenicity of Lip-#3

Figure 8:
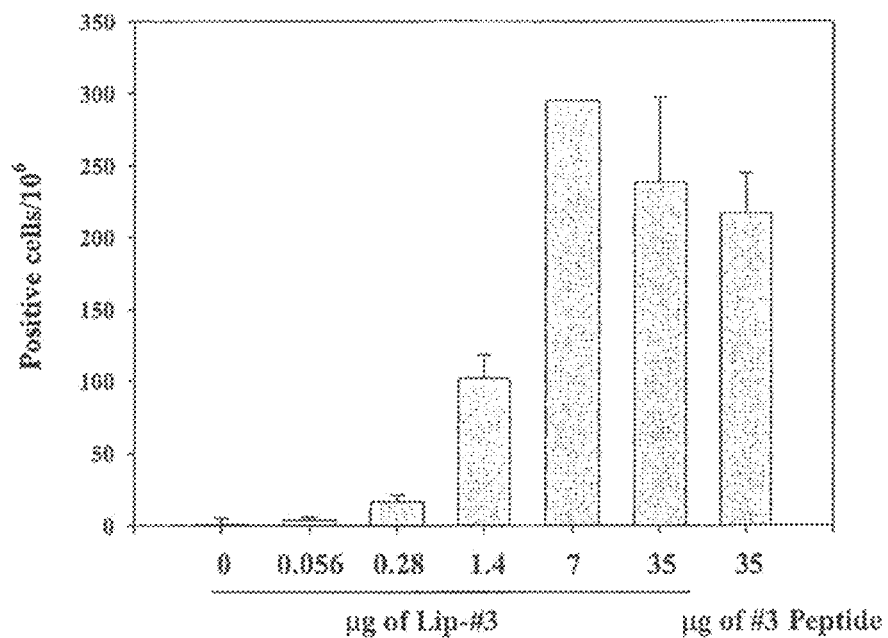
FIG. 8 shows dose dependency of the immunogenicity of Lip-#3.

To study immunogenicity of Lip-#3 in more detail, IFN-γ production was measured by ELISPOT using serially diluted Lip-#3 (FIG. 8). As a result, IFN-γ production could be induced with a trace dose of 0.28 μg, thus showing the superior immunogenicity of Lip-#3 even at an extremely low dose.

Example 6

Cross-Reactivity of Lip-#3

Figure 9:
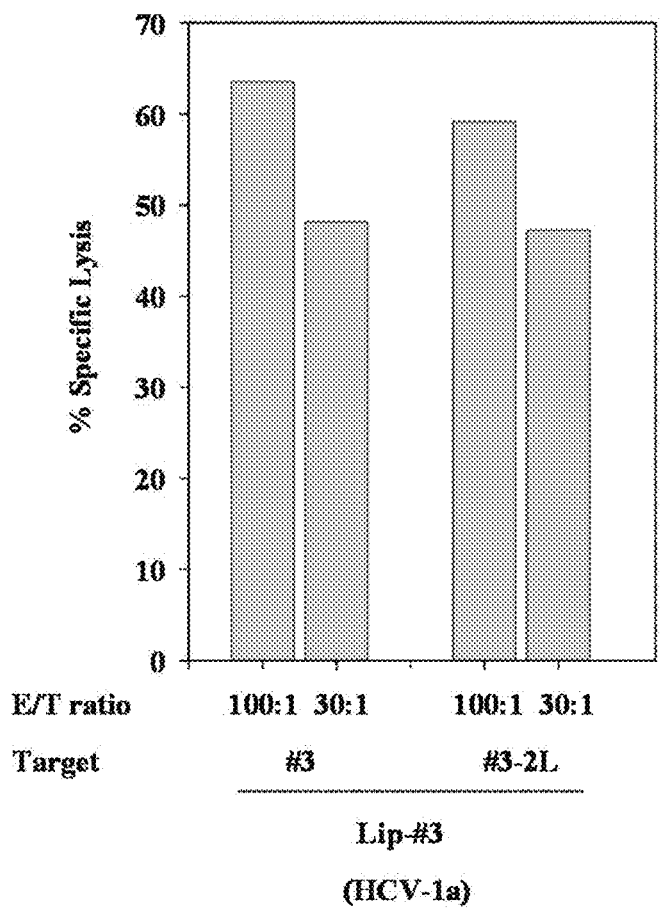
FIG. 9 shows cross-reactivity of Lip-#3.

Peptide #3 is a peptide derived from HCV-1a strain. Whether CTL induced by immunization with Lip-#3 shows reactivity to other peptide derived from HCV strain was examined by a $^{51}$Cr release test (FIG. 9). As a result, immunization with Lip-#3 was found to induce a strong CTL reaction with #3-2L (SEQ ID NO: 4) derived from HCV-1b strain, which is of the same level as the reaction with peptide #3 derived from HCV-1a strain. That is, it was demonstrated that mere immunization with Lip-#3 is expected to provide a vaccine effect on both HCV-1a strain and HCV-1b strain.

Example 7

Cross-Reactivity of Lip-#13 and Lip-#13-1A

Figure 10:
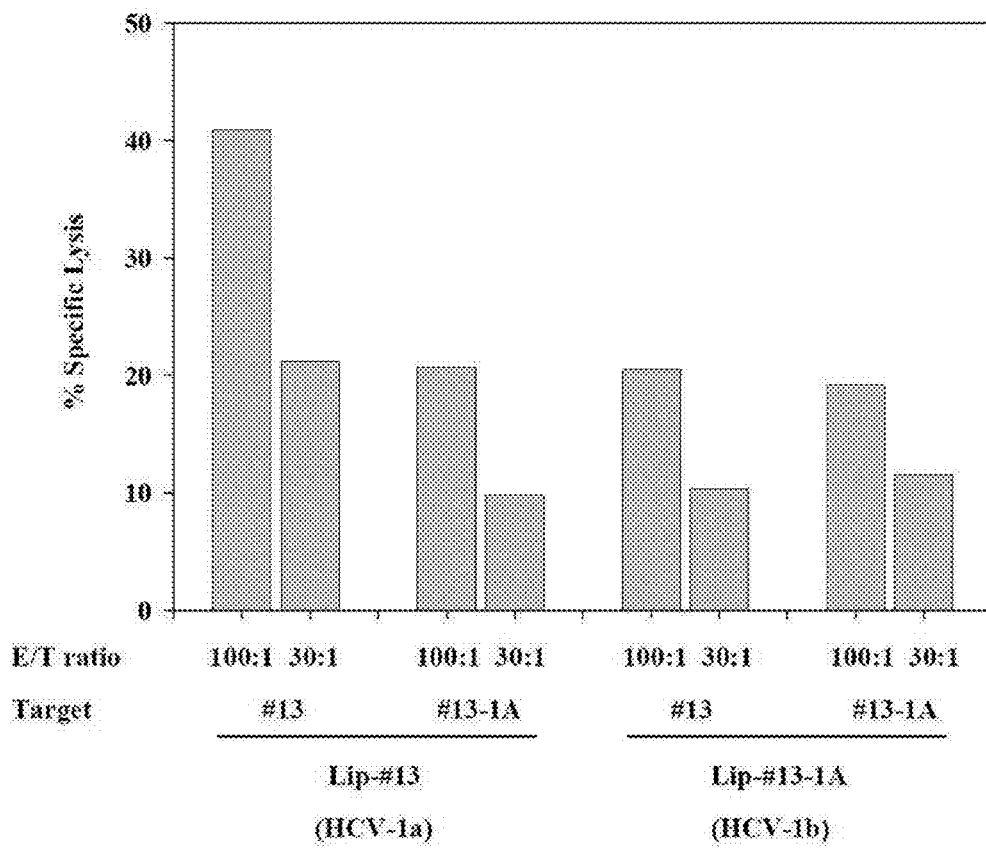
FIG. 10 shows cross-reactivity of Lip-#13 and Lip-#13-1A.

Peptides #13 and #13-1A (SEQ ID NO: 2) are peptides derived from HCV-1a strain and HCV-1b (J1) strain, respectively. In the same manner as in Example 6, the cross-reactivity of Lip-#13 and Lip-#13-1A was examined by $^{51}$Cr release test (FIG. 10). However, a peptide-bound liposome was inoculated twice in the time schedule shown in the lower panel of FIG. 10. It was found that immunization with Lip-#13 also causes a strong CTL reaction with #13-1A, though lower than the CTL reaction with #13. In addition, it was found that immunization with Lip-#13-1A also induces a strong CTL reaction with #13, which is of the same level as the reaction with #13-1A. That is, it was demonstrated that mere immunization with Lip-#13 or Lip-#13-1A is expected to provide a vaccine effect on both HCV-1a strain and HCV-1b (J1) strain.

Example 8

Cross-Reactivity of Lip-#19 and Lip-#19-3A

Figure 11:
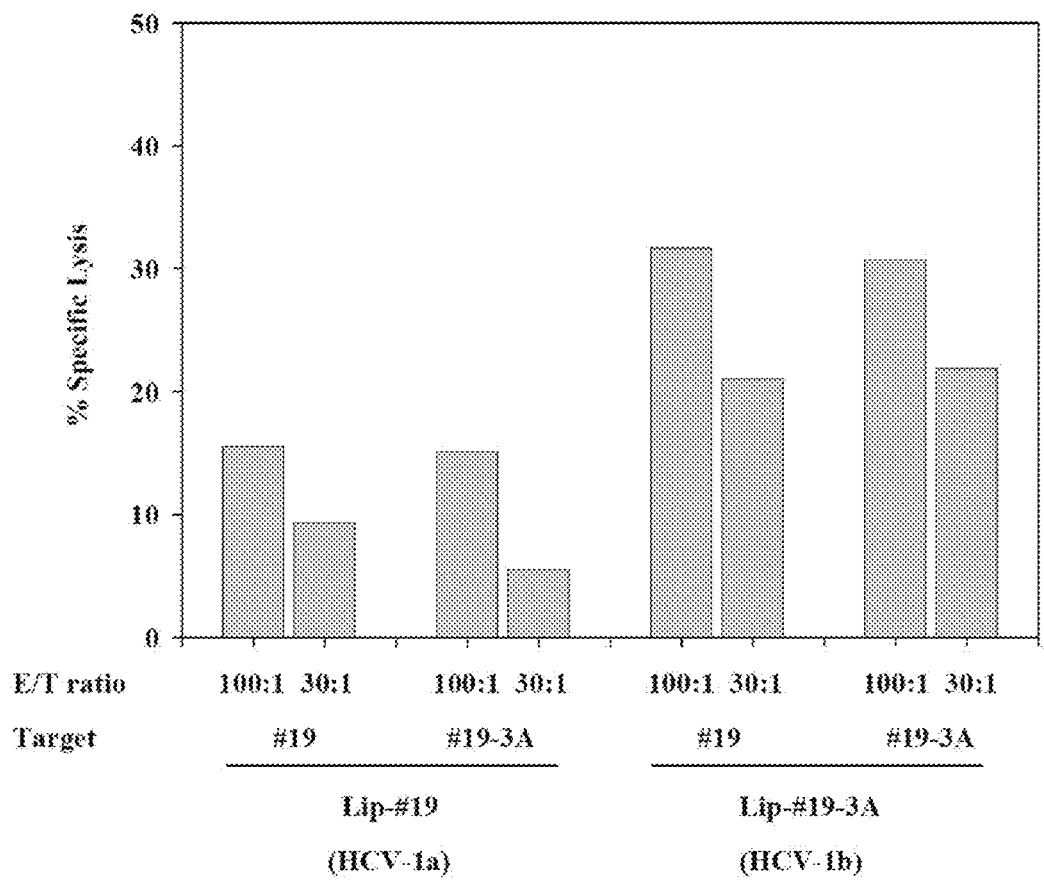
FIG. 11 shows cross-reactivity of Lip-#19 and Lip-#19-3A.

Peptides #19 and #19-3A (SEQ ID NO: 6) are peptides derived from HCV-1a strain and HCV-1b (J1) strain, respectively. In the same manner as in Example 6, the cross-reactivity of Lip-#19 and Lip-#19-3A was examined by $^{51}$Cr release test (FIG. 11). However, a peptide-bound liposome was inoculated twice in the time schedule shown in the lower panel of FIG. 11. It was found that immunization with Lip-#19 also causes a strong CTL reaction with #19-3A, which is of the same level as the reaction with #19. In addition, it was found that immunization with Lip-#19-3A also induces a strong CTL reaction with #19, which is of the same level as the reaction with #19-3A. That is, it was demonstrated that mere immunization with Lip-#19 or Lip-#19-3A is expected to provide a vaccine effect on both HCV-1a strain and HCV-1b(J1) strain. In addition, comparison of #19 and #19-3A revealed that a liposome bound with #19-3A shows a higher vaccine effect.

INDUSTRIAL APPLICABILITY

According to the present invention, a vaccine showing a high effect on hepatitis C virus inherently having low immunogenicity can be provided. Moreover, an effective treatment can also be provided for patients showing a limited effect by conventional treatment methods.

This application is based on a patent application No. 2010-201160 filed in Japan (filing date: Sep. 8, 2010), the contents of which are incorporated in full herein.

The invention claimed is:

1. A method for the prophylaxis or treatment of hepatitis C in a mammal, comprising administering a prophylactically or therapeutically effective amount of a peptide-bound liposome to the mammal,
wherein
the peptide comprises an amino acid sequence selected from the group consisting of SEQ ID NOs: 1-3, 5, and 6, has a length of 9 to 11 amino acids, and induces cytotoxic T lymphocytes,
the liposome comprises a phospholipid containing an acyl group having 14 to 24 carbon atoms and one unsaturated bond or a hydrocarbon group having 14 to 24 carbon atoms and one unsaturated bond, and a liposome stabilizer; and
the peptide is bound to the surface of the liposome.

2. The method according to claim 1, wherein the phospholipid is a phospholipid containing an acyl group having 14 to 24 carbon atoms and one unsaturated bond.

3. The method according to claim 1, wherein the acyl group is an oleoyl group.

4. The method according to claim 1, wherein the phospholipid is at least one selected from diacylphosphatidylserine, diacylphosphatidylglycerol, diacylphosphatidic acid, diacylphosphatidylcholine, diacylphosphatidylethanolamine, succinimidyl-diacylphosphatidylethanolamine, and maleimido-diacylphosphatidylethanolamine.

5. The method according to claim 1, wherein the liposome stabilizer is cholesterol.

6. The method according to claim 1, wherein the peptide is bound to a phospholipid containing an acyl group having 14 to 24 carbon atoms and one unsaturated bond or a hydrocarbon group having 14 to 24 carbon atoms and one unsaturated bond, which phospholipid is contained in a phospholipid membrane constituting the liposome.

7. The method according to claim 1, wherein the liposome has the following composition: (A) a phospholipid containing an acyl group having 14 to 24 carbon atoms and one unsaturated bond or a hydrocarbon group having 14 to 24 carbon atoms and one unsaturated bond 1 to 99.8 mol %; (B) a liposome stabilizer 0.2 to 75 mol %.

8. The method according to claim 1, wherein the liposome has the following composition: (I) an acidic phospholipid containing an acyl group having 14 to 24 carbon atoms and one unsaturated bond or a hydrocarbon group having 14 to 24 carbon atoms and one unsaturated bond 1 to 85 mol %; (II) a neutral phospholipid containing an acyl group having 14 to 24 carbon atoms and one unsaturated bond or a hydrocarbon group having 14 to 24 carbon atoms and one unsaturated bond 0.01 to 80 mol %; (III) a phospholipid containing an acyl group having 14 to 24 carbon atoms and one unsaturated bond or a hydrocarbon group having 14 to 24 carbon atoms and one unsaturated bond, which is bound with a peptide 0.2 to 80 mol %; (IV) a liposome stabilizer 0.2 to 75 mol %.

9. The method according to claim 1, wherein the peptide-bound liposome further comprises CpG-DNA.

10. The method according to claim 1, wherein the partial amino acid sequence is the amino acid sequence of SEQ ID NO: 1.

11. The method according to claim 1, wherein the partial amino acid sequence is the amino acid sequence of SEQ ID NO: 2.

12. The method according to claim 1, wherein the partial amino acid sequence is the amino acid sequence of SEQ ID NO: 3.

13. The method according to claim 1, wherein the partial amino acid sequence is the amino acid sequence of SEQ ID NO: 5.

14. The method according to claim 1, wherein the partial amino acid sequence is the amino acid sequence of SEQ ID NO: 6.

* * * * *